(12) United States Patent
Kosofsky

(10) Patent No.: US 10,660,547 B2
(45) Date of Patent: May 26, 2020

(54) JOINT POSITION ERROR TEST SYSTEMS AND METHODS

(71) Applicant: Cornell University, Ithaca, NY (US)

(72) Inventor: Barry E. Kosofsky, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/518,526

(22) Filed: Jul. 22, 2019

(65) Prior Publication Data
US 2020/0022624 A1    Jan. 23, 2020

Related U.S. Application Data

(60) Provisional application No. 62/702,099, filed on Jul. 23, 2018.

(51) Int. Cl.
| | | |
|---|---|---|
| *A61B 5/00* | (2006.01) | |
| *A61B 5/11* | (2006.01) | |
| *G06T 7/00* | (2017.01) | |
| *G06T 7/70* | (2017.01) | |

(52) U.S. Cl.
CPC .......... *A61B 5/1124* (2013.01); *A61B 5/4064* (2013.01); *A61B 5/4848* (2013.01); *G06T 7/0012* (2013.01); *G06T 7/70* (2017.01); *A61B 5/1128* (2013.01); *A61B 2562/0204* (2013.01);
(Continued)

(58) Field of Classification Search
CPC ....... A61B 5/11; A61B 5/1121; A61B 5/1124; A61B 5/4064; G06T 7/70
See application file for complete search history.

(56) References Cited

U.S. PATENT DOCUMENTS

| | | | |
|---|---|---|---|
| 2012/0089369 A1 | 4/2012 | Abuzeni et al. | |
| 2013/0191068 A1* | 7/2013 | Hess | G01B 21/16 |
| | | | 702/141 |
| 2016/0291688 A1* | 10/2016 | Hirota | G06F 3/14 |

(Continued)

FOREIGN PATENT DOCUMENTS

| | | |
|---|---|---|
| EP | 3 015 056 A1 | 5/2016 |
| WO | WO 2017/137852 A2 | 8/2017 |

OTHER PUBLICATIONS

International Search Report and Written Opinion, issued in Int'l. App. No. PCT/US2019/042799, 10 pages (dated Oct. 15, 2019).

*Primary Examiner* — Max F Hindenburg
(74) *Attorney, Agent, or Firm* — Foley & Lardner LLP

(57) ABSTRACT

Tools and techniques for providing joint position error test system are provided. A system includes a head sensing unit coupled to a joint position error processor. The head sensing unit may include a positional sensor and further be configured to be coupled to the head of a test subject. The joint position error processor may include a processor, and non-transitory computer readable media comprising instructions executable by the processor to record reference sensor data from the positional sensor when the test subject's head is in a reference position, record return sensor data when the test subject's head is in a return position. The instructions may further be executable to determine a position error based on the reference sensor data and the return sensor data, and to further determine the presence of a condition of the test subject based on the position error.

19 Claims, 13 Drawing Sheets

(52) U.S. Cl.
CPC . *A61B 2562/028* (2013.01); *A61B 2562/0219* (2013.01)

(56) References Cited

U.S. PATENT DOCUMENTS

| | | | |
|---|---|---|---|
| 2018/0008141 A1* | 1/2018 | Krueger | A61B 5/744 |
| 2019/0278091 A1* | 9/2019 | Smits | H04N 13/363 |

* cited by examiner

JOINT POSITION ERROR TEST SYSTEMS AND METHODS

CROSS REFERENCE TO RELATED APPLICATIONS

This application claims priority under 35 U.S.C. § 119(e) to U.S. Provisional Patent Application No. 62/702,099, filed Jul. 23, 2018 to Barry E. Kosofsky, entitled "Joint Position Error Test Systems and Methods," the disclosure of which is incorporated herein by reference in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to concussion diagnostic and therapeutic systems, and more specifically to a joint position error test system.

BACKGROUND

Concussion is often a difficult condition to diagnose. One diagnostic technique is the joint position error test, in which the ability of a subject, such as a patient, to return the head to an original orientation after rotating the head axially about the neck is measured. Typically, the test is administered in a subjective fashion, in which a clinician uses their judgment about the orientation of the subject's head, or otherwise mechanically measure the position of a subject's head to evaluate the results of the test.

SUMMARY

In one aspect, a system for implementing a joint position error test is provided. The system includes a head sensing unit and a joint position error processor. The head sensing unit may include one or more positional sensors and may be configured to be coupled to a head of a test subject. The joint position error processor may be coupled to the head sensing unit and further include a processor and non-transitory computer readable media comprising instructions executable by the processor to perform various functions. Accordingly, the joint position error processor may be configured to establish a connection to the head sensing unit, and record, via the head sensing unit, reference sensor data from the one or more positional sensors at a reference position, wherein the reference sensor data is indicative of an orientation of the head of the test subject at the reference position. The joint position error processor may then receive, via the head sensing unit, the reference sensor data. Similarly, the joint position error processor may be configured to record, via the head sensing unit, return sensor data from the one or more positional sensors at a return position, wherein the return sensor data is indicative of the orientation of the head of the test subject at the return position after the test subject has completed rotation of their head and attempted to return their head to the reference position, and again receive, via the head sensing unit, the return sensor data. The joint position error processor may be configured to determine a position error based on the reference sensor data and the return sensor data, wherein the position error is indicative of a deviation of the orientation of the head of the test subject at the return position from the orientation of the head of the test subject at the reference position. Based on the position error, the joint position error processor may determine a presence of a condition of the test subject.

In another aspect, an apparatus for joint position error testing is provided. The apparatus includes a positional sensor configured to generate sensor data indicative of an orientation of a head of a test subject, a processor; and non-transitory computer readable media comprising instructions executable by the processor to perform various functions. The apparatus may be configured to determine that the head of the test subject is in a reference position, and record reference sensor data from the positional sensor, wherein reference sensor data is indicative of the orientation of the head of the test subject in the reference position. The apparatus may further determine that the head of the test subject is in a return position after a rotation has been performed by the head of the test subject, and record return sensor data from the positional sensor, wherein return sensor data is indicative of the orientation of the head of the test subject in the return position.

In further aspect, a method for implementing a joint position error test is provided. The method includes determining, via one or more positional sensors, that the head of a test subject is in a reference position, and recording reference sensor data from the one or more positional sensors, wherein reference sensor data is indicative of the orientation of the head of the test subject in the reference position. The method continues by determining, via one or more positional sensors, that the head of a test subject is in a return position, and recording return sensor data from the one or more positional sensors, where return sensor data is indicative of the orientation of the head of the test subject in the reference position. The method further includes determining a position error based on the reference sensor and the return sensor data, wherein the position error is indicative of a deviation of the orientation of the head of the test subject at the return position from the orientation of the head of the test subject at the reference position, and determining a presence of a condition of the test subject based on the position error.

BRIEF DESCRIPTION OF THE DRAWINGS

A further understanding of the nature and advantages of the embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION

The following detailed description illustrates a few embodiments in further detail to enable the practice of such embodiments. The described examples are provided for illustrative purposes and are not intended to limit the scope of the present disclosure.

Systems, apparatuses, and methods for joint position error test system are detailed herein. In one implementation, a device can include a cap, headband, or other wearable that incorporates, or has affixed thereto, one or more light sources. Lasers of any desired wavelength(s) are typical examples, but light emitting diodes and/or other light sources can be used as well. It should be noted that the light source can emit light outside the visible spectrum. For example, an infra-red light source can be used. This device can be used as a diagnostic for cervico-genic proprioceptive deficits, including conditions resulting from concussion. In some cases, the device can be used as a therapeutic for such conditions as well.

Figure 1:
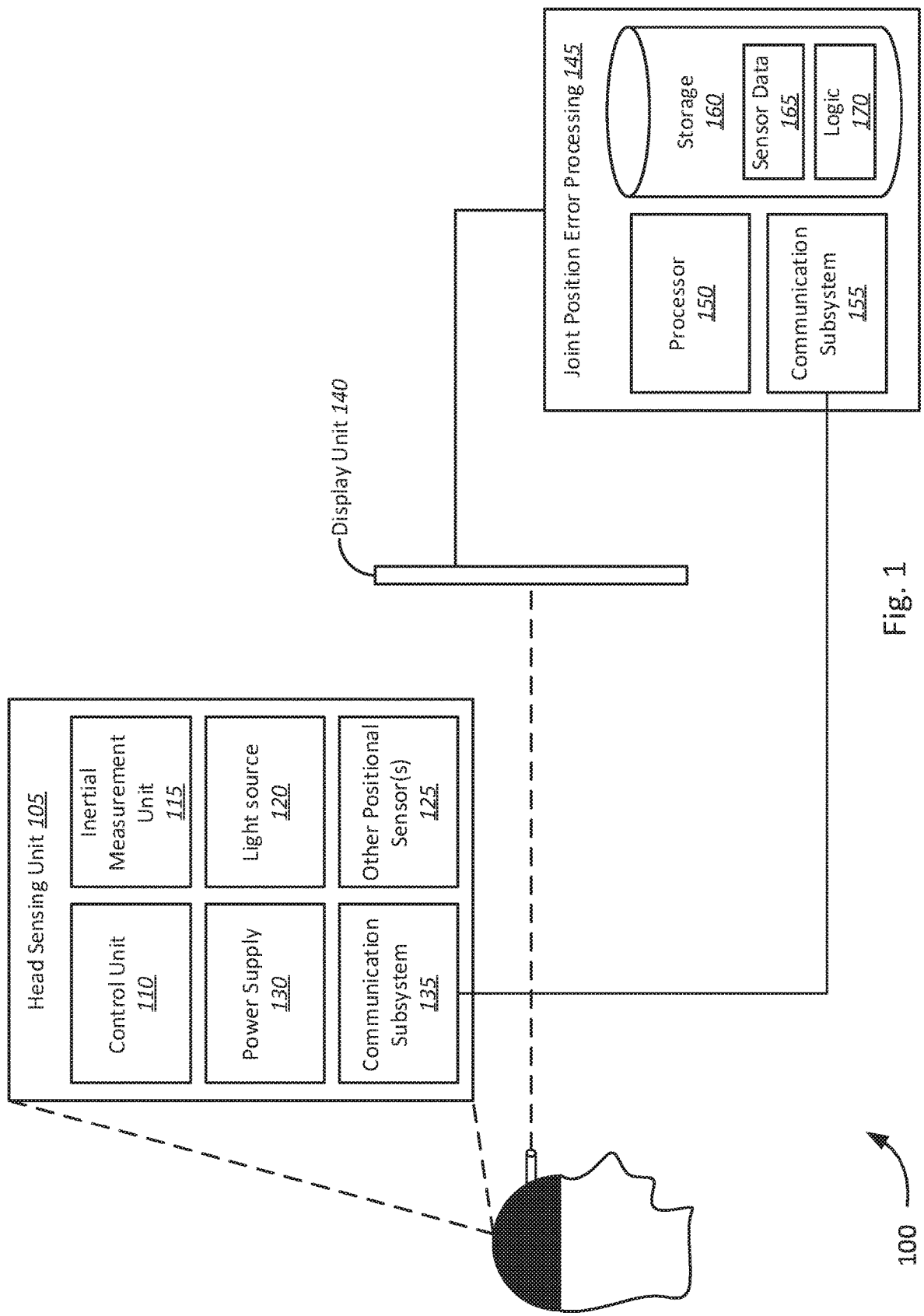
FIG. 1 is a block diagram of a system for implementing a joint position error test, in accordance with various embodiments.

FIG. 1 is a block diagram of a system 100 for implementing a joint position error test, in accordance with various embodiments. The system may include a head sensing unit 105, display unit 140, and joint position error processing unit 145. The head sensing unit 105 may include a control unit 110, inertial measurement unit (IMU) 115, light source 120, one or more other positional sensors 125, power supply 130, and a communication subsystem 135. The joint position error processing unit 145 may include a processor 150, communication subsystem 155, and storage 160, which further includes sensor data 165 and logic 170. It should be noted that the various components of the system 100 are schematically illustrated in FIG. 1, and that modifications to the system 100 may be possible in accordance with various embodiments.

In some embodiments, the head sensing unit 105 may include a control unit 110, coupled to each of the IMU 115, light source 120, and one or more other positional sensors 125, power supply 130, and communication subsystem 135. Power supply 130 may similarly be coupled to each of the control unit, IMU 115, light source 120, one or more other positional sensors 125, and communication subsystem 135. The head sensing unit 105 may be coupled to the joint position error processing unit 145. The joint position error processing unit 145 may include a processor 150 coupled to a respective communication subsystem 155, storage 160, and the display unit 140.

In some embodiments, the head sensing unit 105 may be configured to determine the position and orientation of the head of a test subject (also interchangeably referred to as a patient). In some embodiments, the head sensing unit 105 may be configured to be worn around the head of the test subject. For example, in some embodiments, the head sensing unit 105 may take the form of a cap, hat, balaclava, headband, visor, glasses, or any other suitable wearable form that is configured to maintain a consistent orientation relative to the head of the patient.

The head sensing unit 105 may include various positional sensors, including an IMU 115 and one or more other positional sensors 125, configured to determine the relative orientation of a test subject's head. The one or more other positional sensors 125 may include, for example, gyroscopes (optical, micro-electro-mechanical (MEMs), or other), Bluetooth, Wi-Fi, and other radio frequency (RF) positional sensors, acoustic positional sensors, and other optical sensors (e.g., camera, light emitting diode (LED), infrared (IR), etc.). In some examples, the IMU 115 may be configured to detect angular changes in at least 2 axes. Thus, the IMU 115 may be configured to determine an orientation of the head in at least two planes.

In some embodiments, the light source 120 may be configured to provide visual feedback to the test subject wearing the head sensing unit 105 during operation and/or while a joint position error test is performed. Accordingly, in some embodiments, the light source 120 may be configured to point in the same direction that the test subject's head is facing (e.g., forward). For example, in some embodiments, the light source 120 may be positioned to emit light in a direction that is substantially parallel (e.g., within a grade of 20% grade or less) to the transverse and sagittal planes of the subject's head, and substantially orthogonal (e.g., within a grade of 20% or less) to a coronal plane of the subject's head. In some embodiments, the light source 120 may be configured to emit light such that a visible spot is produced on a target, such as, in this example, the display unit 140. Accordingly, in some embodiments, the light source 120 may be configured to produce a collimated beam of light, which may in turn produce a consistent spot size on the target at a given distance or over a range of distances from the target. The position of the spot on the target may, in turn, indicate a direction and orientation of the subject's head. In some embodiments, the light source 120 may further be configured to project guidance markings, such as shadows or different colored lighting, onto the target. Thus, in some embodiments, the light source 120 may include, for example, a laser light source (e.g., a laser diode), an LED light source, incandescent light source, or any other suitable light source suitable for producing a lighted spot on the target.

In some embodiments, the light source 120 itself may further be configured to provide a signal from which the position and orientation of a test subject's head may be determined. For example, in some embodiments, the target, in this example the display unit 140, may further include a sensor array comprising one or more light sensors. Thus, the location of the beam or visible spot produced by the light source 120 on the target may be detected. In some examples, the light source 120 may produce one beam using visible light to provide visual feedback to the wearer of the head sensing unit, and light outside of the visible spectrum to determine the position or orientation of the subject's head.

The power supply 130 may be configured to provide power to the head sensing unit 105. For example, the power supply 130 may include various power management circuits (e.g., PMICs or other discrete power circuits), configured to provide power to each of the control unit 105, IMU 115, light source 120, other positional sensors 125, and the communication subsystem 135. For example, the light source 120 may include respective driver circuits, which may have different voltage requirements than the driver circuits of the communication subsystem 135, the control unit 110, IMU 115, and one or more other positional sensors 125. Thus, in some embodiments, the power supply 130 may include a battery, voltage converters, regulators, and/or wall power interfaces, as appropriate.

In some embodiments, the control unit 110 may include various suitable control units for controlling the various positional sensors 115, 125, the light source 120, and communicate via the communication subsystem 135. Thus, the control unit 110 may include, for example, a processor, programmable logic controller or other single-board computer, custom integrated circuits (IC) or application specific integrated circuits (ASICs), field programmable gate arrays (FPGA), or other embedded controller solution.

Thus, in some embodiments, the control unit 110 may be configured to obtain sensor data generated by the IMU 115, light source 120, and/or one or more other positional sensors 125, and transmit the sensor data to a joint position error processing unit 145 for further processing (e.g., determination of joint position error). In other embodiments, the control unit 110 may be configured to determine the joint position error on-board the head sensing unit 105 and transmit the results of the determined joint position error to the joint position error processing 145.

In some embodiments, the control unit 110 may be configured to obtain historic or otherwise archived data, collected from other patients or historically from the test subject, and indicative of a normal (expected) range of position error. In some embodiments, the control unit 110 may be configured to obtain the archived data, via the communication subsystem 135, from an external source such as from the joint position error processing unit 145, a server, and/or database. Similarly, the joint position error processing unit may be configured to obtain archived and/or historic data from the control unit 110, or from an external source, such as a server and/or database.

Accordingly, the communication subsystem 135 may be configured to allow the head sensing unit 105 to communicate with external devices. Communication subsystem 135 may include various wired and/or wireless communications systems for networked and/or point-to-point communication. For example, communication subsystem 135 may include, for example, an IR communication device, a wireless communication device and/or chipset (such as a Bluetooth™ device, an 802.11 device, a WiFi device, a WiMax device, a WWAN device, a low-power (LP) wireless device, a Z-Wave device, a ZigBee device, cellular radio, etc.).

Accordingly, in some embodiments, position data may be generated via the use of the IMU 115, light source 120, and/or one or more other positional sensors 125. The target, in turn, may be configured to provide a reference position from which position error may be derived during the joint position error test. As previously described, the target may include a display unit 140. The display unit 140 may be any suitable display for displaying various images and/or video. Thus, the display unit 140 may include, for example, a screen (e.g., liquid crystal display (LCD) panel, LED panel), or a projector and projection screen. The target may be a wall, board (including a lighted board), poster, picture, or other stationary object depicting or otherwise used as a reference position for the joint position error test (e.g., a first position).

In some embodiments, the target (in this example a display unit 140) may further include one or more sensors. For example, the target may include one or more photodetectors for determining a position of a beam projected on the target. In other examples, the one or more other positional sensors 125 of the head sensing unit 105 may include a Bluetooth positional sensor (e.g., transmitter), and the target may include a Bluetooth receiver configured to determine the position and orientation of the head sensing unit 105 via the Bluetooth positional sensor. In further embodiments, the target may include, for example, an acoustic sensor and/or transmitter for determining the position of the head sensing unit 105. It is to be understood that each of the IMU 115, light source 120, one or more other positional sensors 125, and sensors of the target may be used in any combination to determine the position and orientation of the test subject's head.

In some embodiments, the display unit 140 may further be configured to display a target, such as a bullseye, or a representation of the target in examples where the target is separate from the display unit 140. The display unit 140 may further be configured to provide feedback to the test subject regarding a current position of the test subject's head, test results of the joint position error test, current detected location of a light beam relative to the target, among other information. In some embodiments, the display unit 140 may be separate from the target, while in other embodiments, the display unit 140 may both be and/or display a target and configured to provide feedback and information as described above.

In some embodiments, the joint position error processing unit 145 may include a computer system, server, a user device, smartphone, tablet, or other computing device. In further embodiments, the joint position error processing unit 145 may include a single-board computer, microcontroller, FPGA, or custom IC or ASIC. In some embodiments, the joint position error processing unit 145 may be configured to receive, via the communication subsystem 155, sensor data 165 from the head sensing unit 105 and/or a target, such as the display unit 140. Sensor data 165 may include position information from one or more of the IMU 115, one or more other positional sensors 125, or one or more sensors of the target (e.g., a sensor array of the target). In some embodiments, the joint position error processing unit 145 may further be configured to cause the display unit 140 to display feedback and/or other information as previously described, based on the sensor data 165. In some embodiments, the head sensing unit 105 may be coupled to the display unit 140 and configured to cause the display unit 140 to display feedback and/or other information as described above.

In some embodiments, the joint position error processing unit 145 may be configured to cause display unit 140 to display, or to audibly present (e.g., via a speaker), instructions to a test subject for the joint position error test. For example, in some embodiments, the joint position error processing unit 145 may be configured to instruct, via the display unit 140 and/or the speaker, the test subject to align the beam generated by the light source 120, or another visual indicator displayed on the target and/or display unit 140, with an alignment area of the target. In some embodiments, the alignment area may be displayed as a centralized point, spot, or zone, and may further be a different color from the surrounding areas of the target (e.g., within 10 cm of the target). In some embodiments, the alignment area may be arbitrarily chosen based on a resting position of the head of the test of subject. Thus, for example, the alignment area may simply be a starting position from which the joint position error test may be conducted. Once the beam and/or visual indicator has been aligned with the alignment area of the target, the joint position error processing unit 145 and/or the head sensing unit 105 may record, acquire, obtain, or otherwise identify sensor data indicative of a position and orientation of the test subject's head when the beam/visual indicator is in alignment with the target area. This recorded position may be saved as a reference position (e.g., a first position) by the head sensing unit 105 and/or joint position error processing unit 145. In some embodiments, the head sensing unit 105 may record, acquire, obtain, or otherwise identify sensor data at the reference position (also referred to as reference sensor data or first sensor data) and transmit the sensor data at the reference position to the joint position error processing unit 145.

In some embodiments, the head sensing unit 105 and/or joint position error processing unit 145 may be configured to automatically determine when alignment has been reached. For example, in some embodiments, sensor data collected from one or more sensors of the target may be used to determine when a beam of light has been aligned with the alignment area to determine whether alignment has been reached. In some embodiments, the one or more other sensors 125 of the head sensing unit 105 may include a camera, which may visually determine, via image and/or photogrammetric analysis, when the light source 120 and/or the head sensing unit has been properly aligned. In some embodiments, the head sensing unit 105 and/or joint position error processing unit 145 may be configured to determine that alignment has been reached when the patient has stopped moving (or has not exceeded a threshold range of positional change) for a threshold period of time. A clinician and/or the test subject may manually indicate when alignment has been reached via user input to the head sensing unit 105 and/or joint position error processing unit 145.

The joint position error processing unit 145 may further be configured to instruct, via the display unit, the test subject to close their eyes, rotate (or turn) their heads, and return to the first position or reference position (e.g., the position in which the beam and/or visual indicator was aligned with the alignment area). In some embodiments, sensor data may be recorded by the head sensing unit 105 and/or joint position error processing unit 145, when the test subject has reached a maximum angular deviation from the reference position. For example, the furthest absolute angular deviation from the reference position as determined by the sensor data when the subject has turned their head may be recorded or otherwise stored as the maximum angular deviation from the reference position. Sensor data may further be recorded by the head sensing unit 105 and/or joint position error processing unit 145 when the patient has attempted to return to the reference position. The position of the test subject's head after the patient has attempted to the reference position is referred to as the return position or second position. Sensor data recorded at the return position may be referred to as return sensor data or second sensor data. This position may be referred to as the return position. The deviation between the reference position and the return position may be recorded and used as one data point for position error calculation. This process may then be repeated one or more times, automatically or as indicated by a clinician or according to user input (by a clinician and/or the test subject) provided to the joint position error processing unit 145.

As previously described, in some embodiments, the target may include an array of light sensors arranged to determine the position of a beam, generated by the light source 120, that is projected on the target. In some embodiments, the sensor array may be arranged in the pattern of a bullseye. The size of the array may vary, so long as it is able to measure the angular displacement of the test subject's head along at least two planes, (e.g., the transverse plane and sagittal plane of the head). As shown by the dashed line in FIG. 1, the light source emits light, which is received by the sensor array of the display unit. The sensors in the array may include any suitable photodetector, such as photovoltaic cells or other photodiodes, active pixel sensors or other CMOS sensors, charge coupled devices, or the like. Thus, in some embodiments, the target (e.g., display unit 140), sensor array, and/or the cap/light source may further be configured to communicate with joint position error processing unit 145 which may be configured to control the sensor array and/or the head sensing unit 105 (e.g., control unit 110), and/or to receive data from the sensor array and/or head sensing unit 105. Thus, sensors in the target may be utilized to determine a position on the target at a reference position, and to record position data at the returned position. In further embodiments, the light source 120 may be used to provide visual feedback to a user, but position data may be derived from the IMU 115 and/or the one or more other positional sensors 125. For example, IMU 115 position data in the reference position may be recorded and compared to IMU 115 position data in the return position to determine the position error.

In some embodiments, rotation of the test subject's head may further include instructions for transverse rotation. For example, in some embodiments, the patient may be instructed to rotate their head to the left (e.g., look left) and return to an original (e.g., reference) position. Once these steps have been completed and data recorded, the patient may further be instructed to rotate their head to the right (e.g., look right) and return to the reference position. The steps may then be repeated as appropriate to make an accurate diagnosis. In some embodiments, the test subject may further be instructed (by the joint position error processing unit 145, clinician, or other device) to rotate their head in the sagittal plane. For example, the patient may be instructed to rotate their head upwards (e.g., look up) and return to the reference position, and/or rotate their heads downwards (e.g., look down) and return to the reference position. In yet further embodiments, coronal rotation may also be tested. For example, the patient may be instructed to tilt their heads to the left (e.g., move their left ear to their left shoulder) and return to the reference position, and/or to tilt their heads to the right (e.g., move their right ear to their right shoulder) and return to the reference position. Position data may be recorded similarly as described above (e.g., at the reference position, and at the return position). In some embodiments, a combination of transverse, sagittal, and coronal rotation may be tested, sensor data recorded, and respective error determined. For example, in some embodiments, respective sensor data may be recorded, and position error respectively determined for one or more of left transverse rotation, right transverse rotation, upward sagittal rotation, downward sagittal rotation, left coronal rotation, and right coronal rotation.

In some embodiments, the joint position error processing unit 145 and/or head sensing unit 105 may be configured to determine the results of the joint position error test based on an average position error for each return position after each respective rotation. In some embodiments, data for a total of three runs may be collected and average to determine a result. For example, the joint position error processing unit and/or head sensing unit 105 may be configured to determine an average position error (e.g., deviation between the reference position and return position) for three return positions. In some embodiments, an average position error may further respectively be determined for one or more of left transverse rotation, right transverse rotation, upward sagittal rotation, downward sagittal rotation, left coronal rotation, and right coronal rotation.

In some embodiments, a respective reference position may be determined for each "test run." In other words, alignment with an alignment area of the target may be performed each time after a return position has been reached and before a rotation is performed by the test subject. In some further embodiments, the head sensing unit 105 may be configured to indicate that a return position has been reached based on manual input by the test subject and/or clinician (e.g., an input provided to the head sensing unit 105 and/or joint position error processing system 145). In some embodiments, the head sensing unit 105 may be configured to automatically indicate that a return position has been reached based on detecting that the test subject has not moved (or has not exceeded a threshold range of positional change) for a threshold period of time.

In some embodiments, the system 100 may further be configured to therapeutically treat certain conditions, including without limitation those diagnosed by the system. For example, the subject can be directed to point the laser at certain points, in order to improve head/neck/eye coordination. Various embodiments can provide functionality to facilitate such treatment.

For example, with regard to FIG. 1, the target and/or display unit 140 may include a plurality of indicators (such as colored LED's, etc.) that can be selectively activated to indicate to the subject where the laser should be aimed. In an aspect, the head sensing unit 105 and/or the joint position error processing unit 145 may be in communication with the plurality of indicators. In this way, the therapy may be controlled by the clinician and/or or automatically by the head sensing unit 105 and/or the joint position error processing unit 145. In some embodiments, the target and/or display unit 140 may be configured to display a pattern, path, indicator (e.g., a directional arrow, a dot to track, etc.), or otherwise guide one or more movements to be made by patient's head. As previously described, the head sensing unit 105 may be configured to project a beam onto the target to produce a visible spot on the target and/or display unit 140 may be configured to display a visible spot indicative of the position of the test subject's head. Thus, in some examples, the test subject may be directed to follow a movement guide. The movement guide may include, for example, a path, indicator, and/or pattern to be followed and/or traced with the spot produced on the target and/or display unit 140 by the light source 120.

In some embodiments, the ability of the test subject to follow the movement guide may be determined by the head sensing unit 105, one or more sensors of the target and/or display unit 140, or joint position error processing unit 145. In some embodiments, how well a test subject follows it may be determined how closely the visible spot tracks the pattern and/or path. For example, one or more performance metrics may be determined, including, without limitation, whether the visible spot deviates from the movement guide beyond a threshold range of deviation, a maximum deviation, average deviation, range, time to complete, or other suitable metrics. For example, in some embodiments, deviations from a path may be determined as orthogonal deviation from the position of the path. For example, for a horizontal (left/right) path, vertical deviation (up/down) from the horizontal path may be determined. For irregularly shaped paths, orthogonality may be determined based on orthogonality from a line between two sequential points of the path. In some embodiments, an absolute deviation may be determined relative to a point. In some embodiments, absolute deviation may be determined relative to the position of a point that may change over time. In some further embodiments, the one or more performance metrics may be determined in substantially real-time (e.g., within 10 seconds). In some embodiments, the one or more performance metrics may be determined according to a polling rate, or a recording rate of a respective camera (e.g., for each frame and/or image recorded).

Accordingly, in some embodiments, the head sensing unit 105 may include a camera configured to determine a position of the visible spot relative to the movement guide. For example, the camera of the head sensing unit 105 may be configured to determine the one or more performance metrics photogrammetrically (e.g., via image and/or video analysis). In some examples, the head sensing unit 105 may be configured to determine pixel distances (e.g., deviation) between the visible spot and a movement guide.

In some embodiments, an external camera may be utilized to determine the one or more performance metrics photogrammetrically. For example, a visible spot projected by the head sensing unit 105 and/or generated on the display unit 140 based on a position of the head sensing unit 105 may be recorded by the camera. Thus, in some embodiments, a user device, such as a test subject's smart phone, may be utilized to capture video and/or images of the visible spot and movement guide. In other embodiments, a camera may be coupled to the joint position error processing unit 145. In some embodiments, a user device may further be configured to perform photogrammetric analysis of the video and/or images captured by the camera to determine the one or more performance metrics, as described above. In some embodiments, the joint position error processing unit 145 may be configured to determine, photogrammetrically, the one or more performance metrics as described above.

In some embodiments, as previously described, the target or display unit 140 may further comprise one or more sensors configured to determine a position of the visible spot on the target or display unit 140. In some embodiments, the target or display unit 140 may be coupled to the joint position error processing unit 145 and/or an end-user device configured to cause the target or display unit 140 to display the movement guide. Thus, the joint position error processing unit 145 (or an end-user device) may compare the known position of the movement guide relative to the detected position of the visible spot to determine the one or more position metrics. In yet further embodiments, the joint position error processing unit 145 and/or end-user device may be coupled to the IMU 115 and/or one or more other positional sensors 125, and further be configured to determine the one or more position metrics based on sensor data reported by the IMU 115 and/or one or more other positional sensors.

In some embodiments, various components of the system 100 may further be configured to provide feedback, based for example, on the efficiency of the subject at following the progress of the indicators. For instance, an app on a smartphone or other device in communication with the head sensing unit 105 and/or joint position error processing unit 145, display unit 140, or plurality of indicators on a target, may be configured to display feedback (e.g., in the form of different colors, such as green for good, yellow for marginal, red for poor) on the subject's efficiency at navigating a pattern displayed on the target. The in some embodiments, the feedback may be provided based on the one or more performance metrics.

The plurality of indicators may also be configured to provide feedback to the subject and/or the clinician. For example, an indicator can light a certain color (e.g., red) to indicate that the light source 120 should be aimed at that indicator, and when a sensor near that indicator senses the light source 120, the indicator can turn a different color (e.g., green) to indicate success. Correspondingly, another indicator in a different location can light to the certain color, indicating a new target for the light source 120.

In some embodiments, system 100 may further be configured to monitor the efficacy of the therapy, and/or the subject's progress resulting from the therapy. Accordingly, in some embodiments, the joint position error processing unit 145, head sensing unit 105, and/or a user device may be configured to store and/or obtain historic performance data associated with the test subject. The historic performance data may include one or more performance metrics determined based on previous therapeutic sessions. In one example, a historic measure of average deviation may be compared against an average deviation of a current therapeutic session. In other embodiments, other historic performance metrics may be compared to determine whether a patient has improved over time. In some embodiments, the joint position error processing unit 145, head sensing unit 105, and/or a user device may further be configured to track progress over time. Thus, trends and patterns may further be presented to a clinician and/or a user such as the test subject.

Figure 2A:
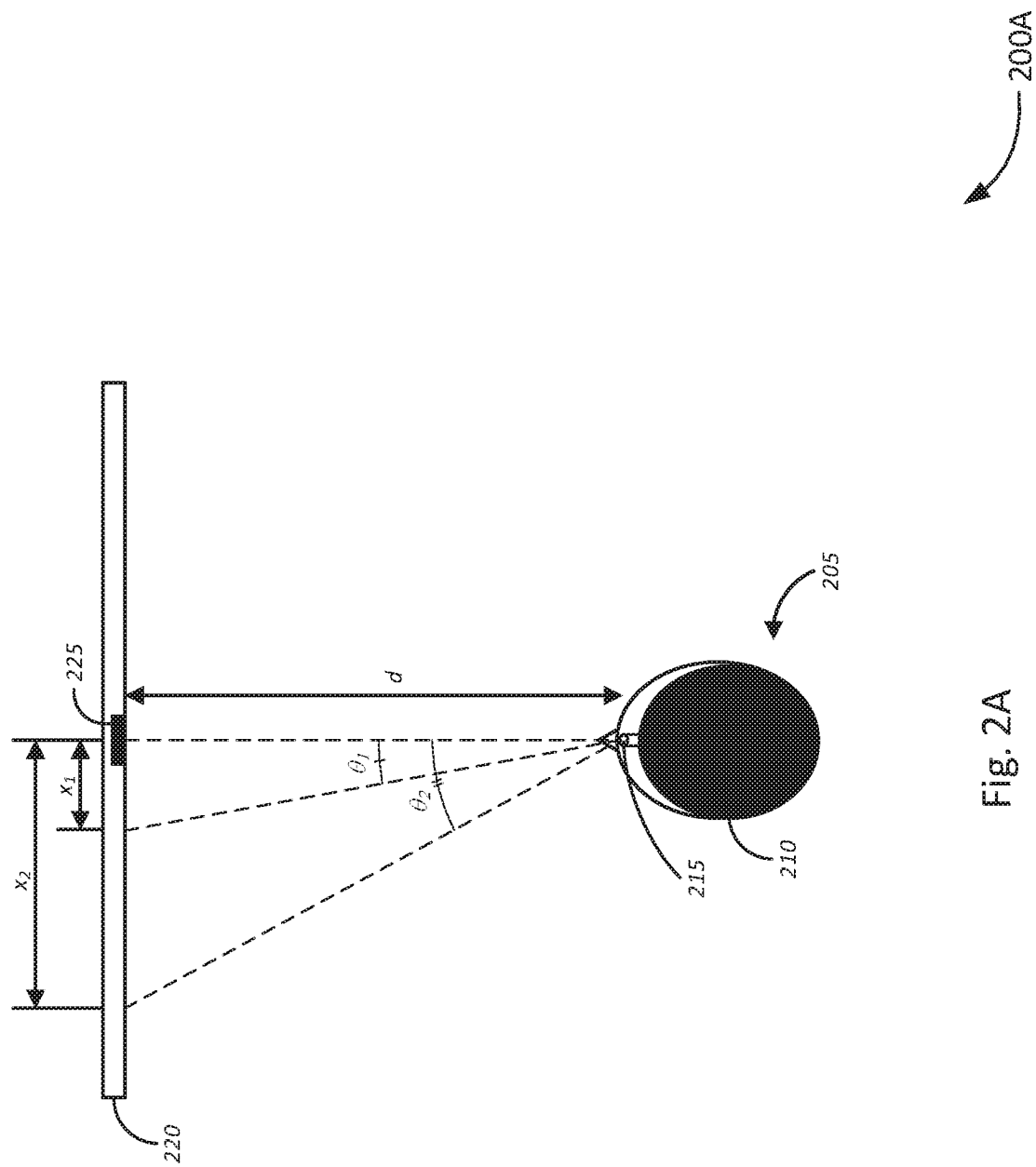
FIG. 2A is a schematic plan view depicting transverse angular displacement during a joint position error test, in accordance with various embodiments.
Figure 2B:
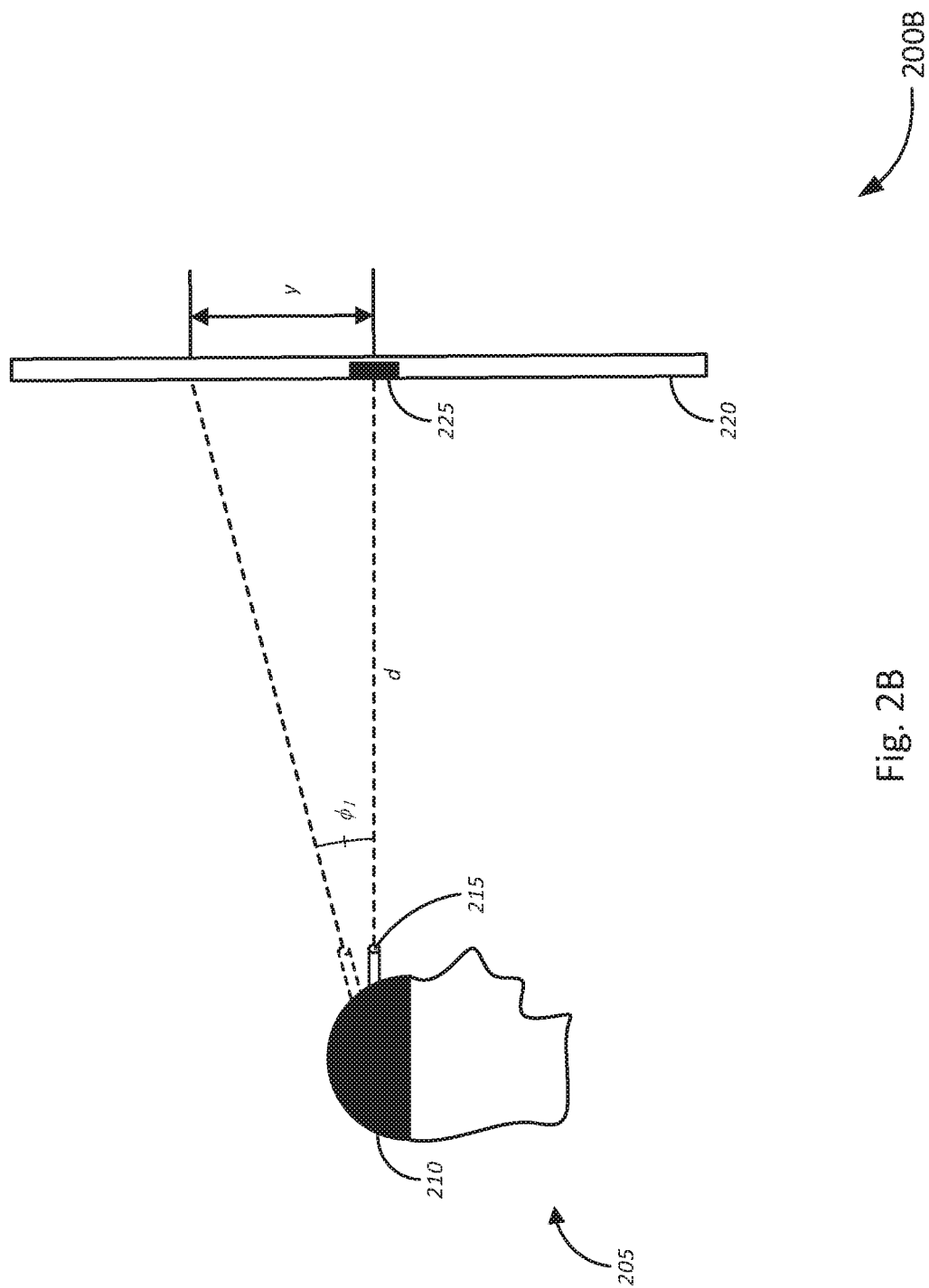
FIG. 2B is a schematic side elevation view depicting sagittal angular displacement during a joint position error test, in accordance with various embodiments.
Figure 2C:
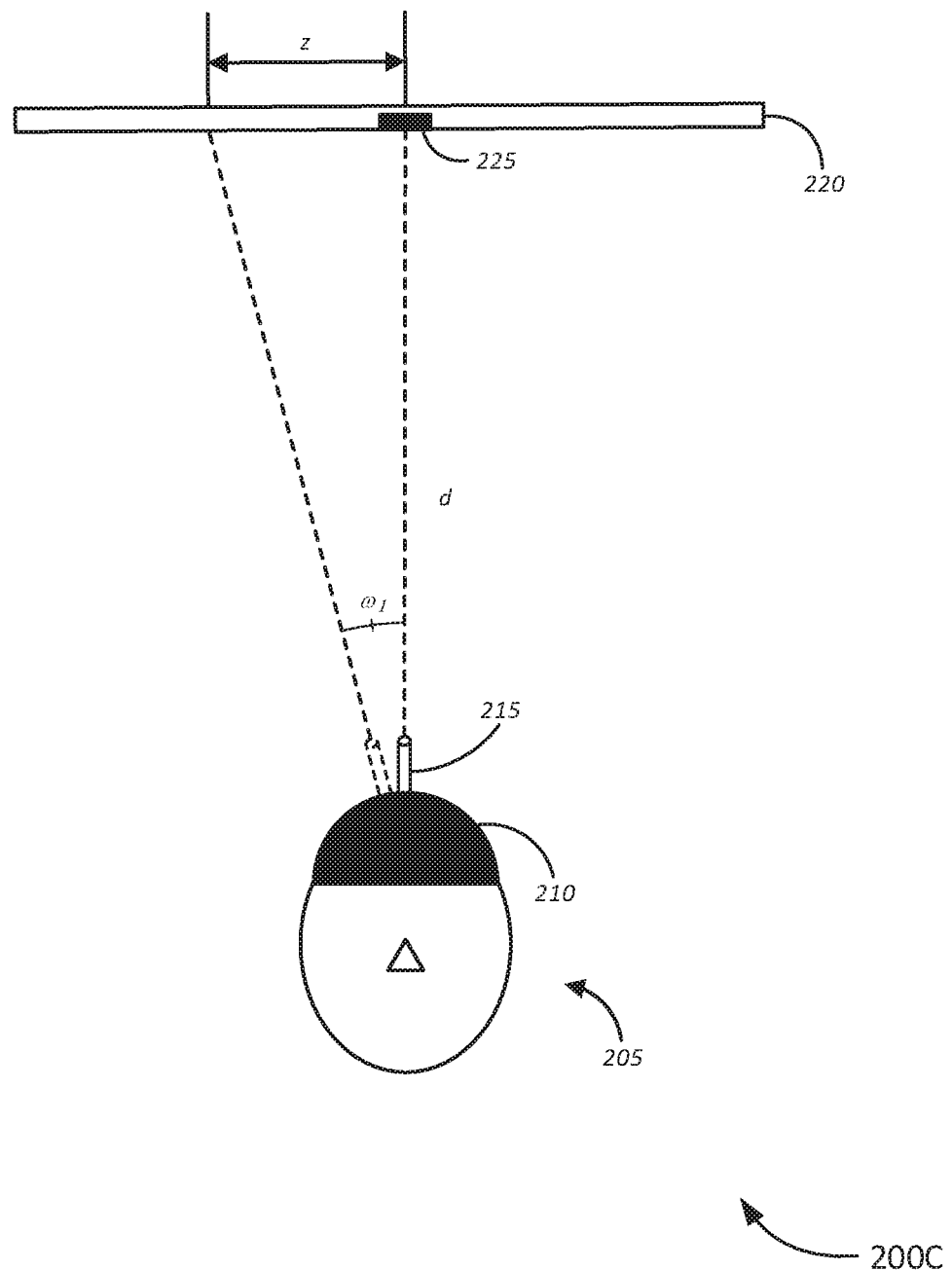
FIG. 2C is a schematic front elevation view depicting coronal angular displacement during a joint position error test, in accordance with various embodiments.

FIGS. 2A-2C respectively depict views 200A-C of transverse angular displacement, sagittal angular displacement, and coronal angular displacement of a test subject's head 205 during the joint position error test. The head sensing unit 210 may include light source 215, and target 220 with alignment area 225. The distance between the test subject's head 205, and specifically the light source 215, is indicated by distance d.

In FIG. 2A, the transverse angular displacement may be given by $\theta_1$ and $\theta_2$. For example, $\theta_1$ may be the angular displacement (from the reference position) at a first return position during a first run, and $\theta_2$ may correspond to the angular displacement at a second return position during a second run. The lateral displacement from the reference position may be given by $x_1$ and $x_2$, respectively corresponding to the lateral displacement of the first and second return positions from the reference position. Accordingly, the angular displacement θ may be given by:

$$\theta = \arctan(d/x)$$

Similarly, in FIG. 2B, the sagittal angular displacement is given by $\phi_1$, which may be the angular displacement from the reference position at a return position. The vertical displacement from the reference position may be given by y, corresponding to the vertical displacement of the return position from the reference position. Thus, the angular displacement φ may be given by:

$$\varphi = \arctan\left(\frac{d}{y}\right)$$

In some embodiments, sagittal angular displacement may also be measured during a transverse rotation test. Similarly, transverse angular displacement may also be measured during a sagittal rotation test. In some embodiments, both lateral and vertical displacement may also be considered to determine a total angular displacement from the reference position (e.g., vertical or coronal plane in front of the patient or substantially parallel with a target (e.g., within a 10% grade)). For example, in some embodiments, a total angular displacement may be given by:

$$\text{Total Angular Displacement} = \arctan\left(\frac{y}{x}\right)$$

Similarly, an absolute displacement (e.g. total distance from the reference position) may be given by:

$$\text{Absolute Displacement} = \sqrt{x^2 + y^2}$$

In FIG. 2C, the coronal angular displacement may be given by $\omega_1$, which may be the angular displacement from a reference position during a coronal rotation test. Lateral displacement from the reference point may be given by z. Thus, the angular displacement ω may be given by:

$$\omega = \arctan\left(\frac{d}{z}\right)$$

In some embodiments, coronal angular displacement may also be measured during a sagittal rotation test. Similarly, coronal angular displacement may also be measured during a sagittal rotation test. Accordingly, In some embodiments, both lateral displacement z and vertical displacement y may also be considered to determine a total angular displacement from the reference position (e.g., horizontal or transverse plane).

Similarly, in some embodiments, coronal angular displacement may also be measured during a transverse rotation test. In addition, coronal angular displacement may also be measured during a transverse rotation test. In some embodiments, both lateral displacement x and z may also be considered to determine a total angular displacement from the reference position in the sagittal plane.

Figure 3A:
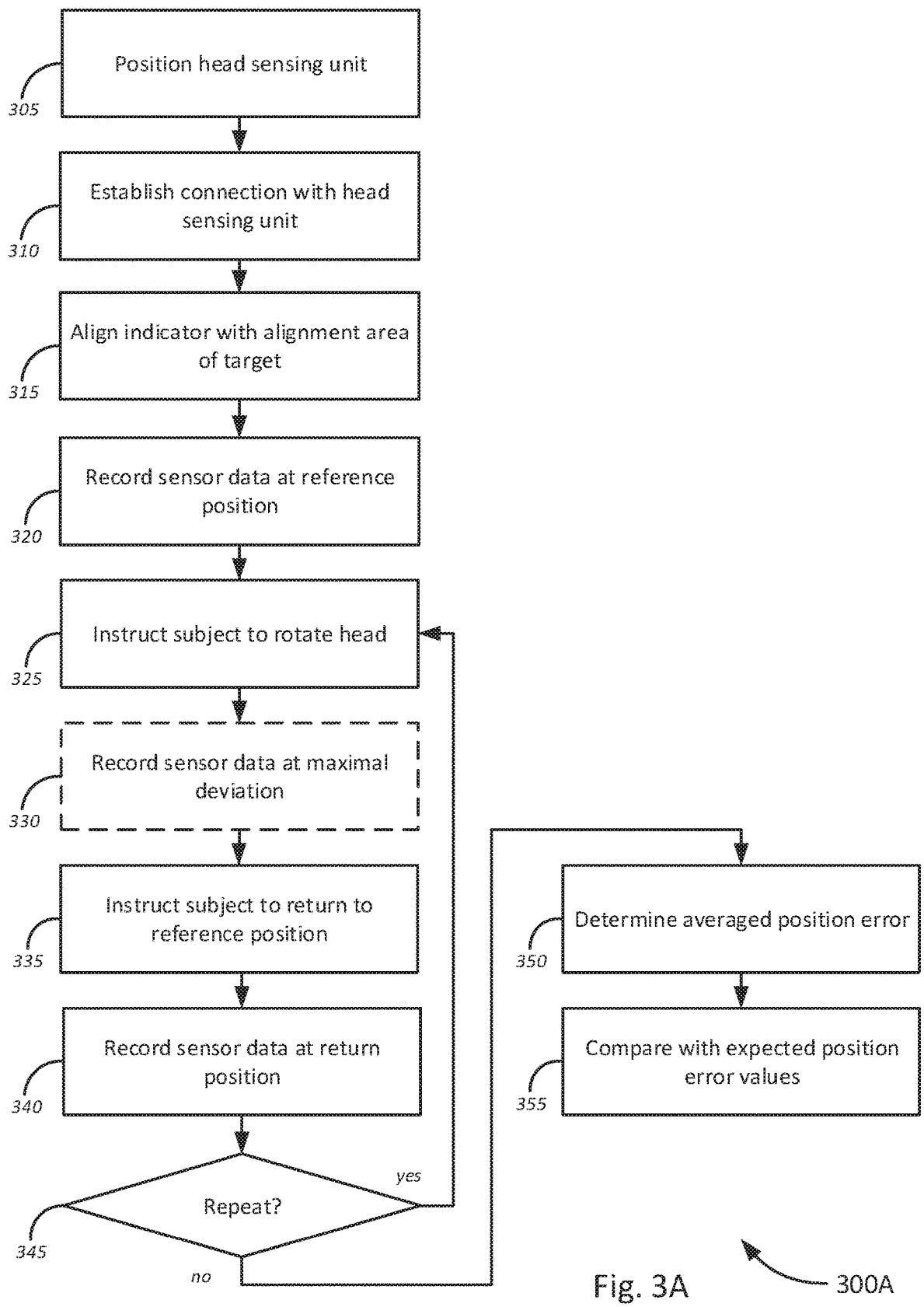
FIG. 3A is a flow diagram of a method of implementing a joint position error test, in accordance with various embodiments.

FIG. 3A is a flow diagram of a method 300A of implementing a joint position error test, in accordance with various embodiments. In some cases, the method may be implemented by software (e.g., computer instructions) stored on a non-transitory computer readable medium and/or executed by a computer system, such as the head sensing unit 105 and/or joint position error processing unit 145 as described above.

At block 305, the method 300A may include positioning the head sensing unit on a test subject's head. As previously described, the head sensing unit may be positioned on a head of the test subject such that a light source and/or other positional sensor points in substantially the same direction (e.g., within 10% in angle) that the head of a test subject is facing. At block 310, the method 300A continues by establishing, with the joint position error processing unit, a connection with the head sensing unit. As previously described, the connection may be a network connection and/or a point-to-point connection between the head sensing unit and a joint position error processing unit. Similarly, a connection may further be established with one or more positional sensors of the target, in supporting embodiments.

At block 315, the method 300A may include aligning an indicator with an alignment area of the target. In some embodiments, the head sensing unit, joint position error processing unit, and/or one or more sensors of a target may be configured to determine whether an indicator has been aligned with an alignment area of the target. As previously described, the target may include an alignment area with which an indicator is to be aligned, and the position of the test subject's head (e.g., position of the head sensing unit) when alignment has been reached may be recorded, at block 320, as the reference position. Thus, in some embodiments, the alignment area may be an area within the target (e.g., the center of a bullseye target) to which the indicator should be aligned. The indicator may include, for example, a visible spot projected onto target, and generated by projecting a beam from a light source of the head sensing unit onto the target. The indicator may be an indicator generated on display unit, such as a smart phone, tablet, monitor, projection, or other screen on which an indicator is displayed indicative of a position and/or orientation of the head sensing unit relative to the target or alignment area. Thus, at block 320, in response to determining that the indicator has been aligned with the alignment area of a target, the sensor data may be recorded at the reference position (e.g., when alignment has been reached).

The method 300A may include block 325 by instructing the test subject to rotate their head. As previously discussed, the subject may be instructed by visual instructions and/or audio instructions delivered by a clinician, a display device, head sensing unit itself, and/or the joint position error processing unit. At optional block 330, sensor data may again be recorded when maximal deviation from the reference position has been reached by the test subject's head (e.g., a position at which the sensor data reaches an absolute maximum deviation from a reference position during the test). In some embodiments, the head sensing unit and/or joint position error processing unit may further be configured to determine whether a subject has sufficiently rotated their heads past a threshold amount, such as 90 degrees from the reference position. The amount of this rotation may be tracked by the joint position error processing unit and/or head sensing unit and recorded, at optional block 330, and an indication given (such as an audio tone) of when the subject's head has rotated sufficiently.

At block 335, the test subject may be instructed to return their head to the reference position. At block 340, sensor data may be recorded once it has been determined that the test subject has reached the return position. As previously described, the head sensing unit and/or joint position error processing unit may be configured to determine if or when the test subject has reached the return position, and in response, to record sensor data at the return position. After the subject has attempted to return the head to the initial orientation, the head sensing unit and/or joint position error processing unit may be configured to analyze the recorded sensor data. For example, from the sensor data at the reference position and sensor data at the return position, one or more of the lateral displacement x, vertical displacement y, and/or lateral displacement z, transverse angular displacement $\theta$ (yaw), sagittal angular displacement $\phi$ (pitch), coronal angular displacement $\omega$ (roll), total angular displacements, and absolute displacements may be determined, as described above.

At decision block 345, the method 300A may include determining whether to repeat another run of the test by having the patient rotate their heads again. If it is determined that the test should be repeated, the method 300A again, at block 325, instructs the test subject to rotate their head, and proceed as previously described.

If it is determined that the test should not be repeated, the method 300A may include, at block 350, determining an averaged position error as previously described. For example, the averaged position error may include one or more position errors as determined respectively for left transverse rotation, right transverse rotation, upward sagittal rotation, downward sagittal rotation, left coronal rotation, and right coronal rotation, among others.

At block 355, the joint position error processing unit may compare the averaged position error values with expected and/or normal position error values. As previously described, historic and/or archived data, collected from their patients or historically from the test subject, and indicative of a normal (expected) range of position error may be obtained from an external source, such as a server and/or database, or may be stored locally on a head sensing unit and/or joint position error processing unit. In some embodiments, the joint position error processing unit may determine a deviation between the measured average position error and the expected position error values. In some embodiments, the joint position error processing unit may be configured to predict the probability and/or diagnose the occurrence of a concussion in the test subject based on the deviation from the expected or normal position error values. For example, the magnitude of total angular displacement can be compared with data from similar subjects (e.g., similar sex, age, body composition, etc.) who had either a positive or negative diagnosis of whatever condition (e.g., concussion) the test is designed to diagnose. Accordingly, in some embodiments, the joint position error processing unit may be configured to obtain empirical data from which the expected or normal position error values may be determined. In some embodiments, the joint position error processing unit may obtain the empirical data from a local or remote database.

Based on the comparison, the joint position error processing unit may determine a condition of the test subject. The condition may indicate, for example, a presence or an absence of a concussion in the test subject. In some embodiments, the joint position error processing unit may determine whether the deviation between the measured average position error and the expected position error values is greater than a threshold. The threshold may demarcate or indicate a margin of difference in the position error values at which to determine the presence or absence of the condition (e.g., concussion). If the deviation is determined to be less than the threshold, the joint position error processing unit may determine that the lack of the condition. Conversely, if the deviation is determined to be greater than or equal to the threshold, the joint position error processing unit may determine that the presence of the condition. In some embodiments, the joint position error processing unit may be configured to include a lookup table (LUT) to lookup joint position error values obtained from the patient. The LUT may contain entries for known joint position error values and corresponding empirically derived probability that a patient having the corresponding joint position error value has the known condition (e.g., a concussion). The joint position error processing unit may determine a probability that the test subject has a respective condition using the LUT.

Figure 3B:
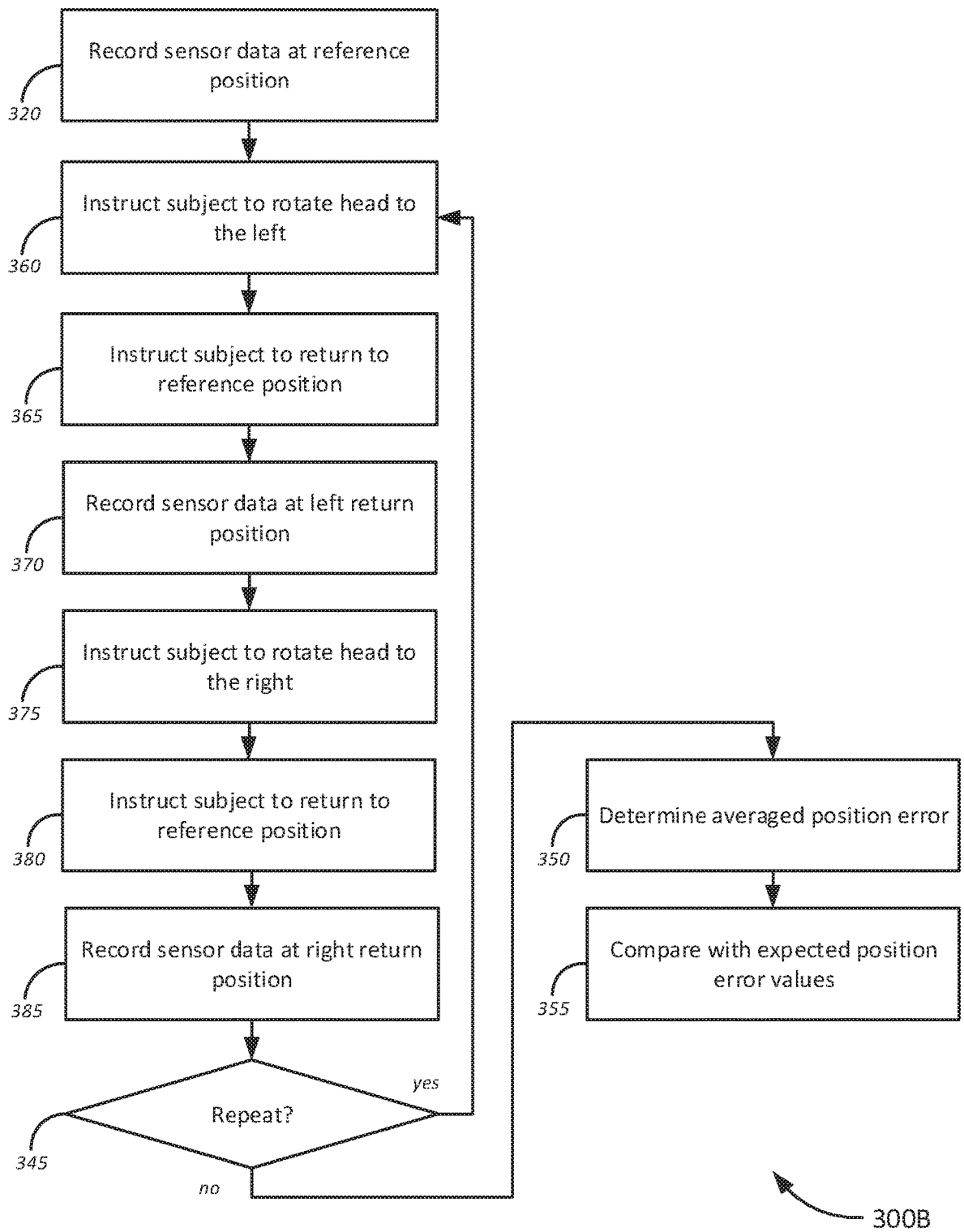
FIG. 3B is a flow diagram of a method of implementing a joint position error test for transverse rotation, in accordance with an embodiment.

FIG. 3B is a flow diagram of a method 300B of implementing a joint position error test for transverse head rotation, in accordance with various embodiments. The method 300B may include some of the same steps as in the method 300A, which may be labeled using the same reference numerals. For example, the method 300B may include, after recording sensor data at the reference position at block 320, instructing the subject to rotate their head to the left, at block 360. As previously described, the head sensing unit and/or joint position error processing unit may be configured to instruct the test subject to look to the left. At block 365, the test subject may further be instructed to return their head to the reference position. At block 370, the head sensing unit and/or joint position error processing unit may record sensor data at the return position. The return position after a left transverse rotation may be referred to as the left return position. At block 375, the process may be repeated for a right transverse rotation, by instructing the subject to rotate their head to the right. At block 380, the test subject may then be instructed to return their head to the reference position. At block 385, the method 300B may include recording sensor data at the right return position (e.g., the return position after a right transverse rotation).

At block 345, the method 300B may include, as in method 300A, determining whether to repeat the transverse head rotation test. At block 350, an averaged position error may be determined. In this case, the averaged position error may include, respectively, an averaged position error or each of the left return position and right return position. For the left return position, one or more of an averaged left angular displacement, averaged left lateral displacement, averaged left total angular displacement, averaged left absolute displacement may be determined. Similarly, for the right return position, one or more of an averaged right angular displacement, averaged right lateral displacement, averaged right total angular displacement, averaged right absolute displacement may be determined. At block 355, the joint position error processing unit may compare the averaged position error values with expected and/or normal position error values, and to predict the probability and/or diagnose the occurrence of a concussion as previously described.

Figure 3C:
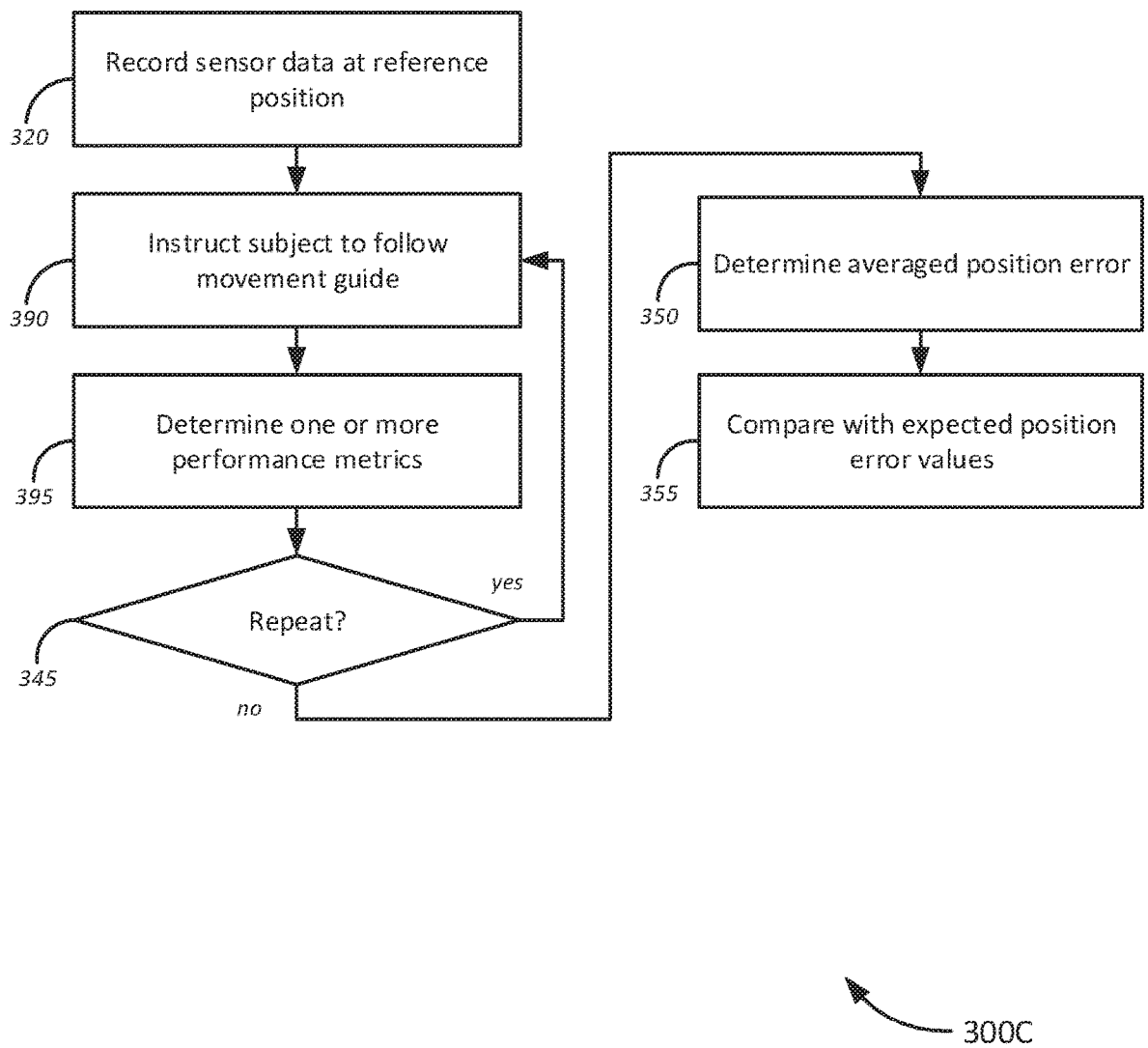
FIG. 3C is a flow diagram of a method of implementing a therapeutic exercise, in accordance with an embodiment.

FIG. 3C is a flow diagram of a method 300C of implementing a therapeutic exercise, in accordance with various embodiments. The method 300C may include some of the same steps as in the method 300A, which may be labeled using the same reference numerals. For example, at block 320, the method 300C may include recording sensor data at the reference position. At block 325, the method 300C may include instructing the subject to follow the movement guide at block 390. As previously described, the movement guide may include, for example, a path, pattern, or indicator configured to indicate a movement to be made by the test subject. As previously described, the movement indicated by the movement guide may include, for example, following a displayed path, tracing a pattern, and/or following an indicator with a visible spot, produced on the target, indicative of the position of the test subject's head.

At block 395, the method 300C includes determining one or more performance metrics. As previously described, performance metrics may include whether the visible spot deviates from the movement guide beyond a threshold range of deviation, a maximum deviation, average deviation, range, time to complete, or other suitable metrics. In some embodiments, the performance metrics may be derived photogrammetrically, through image and/or video analysis, through images recorded by a camera. The performance metrics may be determined by one or more of the head sensing unit, a joint position error processing unit, or a user device. Furthermore, the one or more performance metrics may be determined according to a polling rate, at the recording rate of the camera (e.g., for each video frame or image captured by a camera), or at one or more "checkpoints." For example, in some embodiments, the movement guide may include one or more checkpoints assigned to certain parts of the movement guide. The head sensing unit, joint position error processing unit, or a user device may be configured to determine the one or more performance metrics relative to the "checkpoint." For example, a path may be displayed, with checkpoints at a midway point, and an endpoint of the path. In some embodiments, the path may be a horizontal line (e.g., left to right from the point of view of the test subject). When the lateral position (e.g., position on the horizontal axis) of the visible spot reaches the same lateral position for a corresponding checkpoint, a deviation in an orthogonal direction (e.g., a vertical deviation) may be determined between the visible spot and checkpoint. Accordingly, at each checkpoint, the one or more performance metrics may be determined relative to a position of checkpoints.

At block 345, the method 300C may include determining whether to repeat the therapeutic movement exercise. At block 350, an averaged position error (e.g., an average of one or more of the performance metrics) may be determined over the number of times the therapeutic exercise was completed. At block 355, the joint position error processing unit may compare the averaged position error values with expected and/or normal position error values, and to predict the probability and/or diagnose the occurrence of a concussion as previously described.

By determining the position error to determine the condition (e.g., concussion), the system 100 and methods 300A-C may provide a more accurate result compared to techniques relying on subjective evaluation and/or manual, mechanical measurement by a clinician. For example, the system 100 provides the ability to more accurately measure head position utilizing positional sensors, such as the IMU, and/or visually using a light source. The system 100 also provides the ability to provide consistent data between runs through the use of a measurable reference position, as opposed to a static reference position, or subjectively determined reference position, from which a clinician manually measures data. For instance, the patient's actual head position at the "reference position" may vary between runs, but may be treated by the clinician as if starting from the same reference position at each run. Because of these considerations in determining the reference position, the system 100 and method 300A-C may provide the ability to provide more accurate results for each respective run.

Furthermore, sensors 125 of system 100 may be utilized both in close proximity to the test subject's head (e.g., through the head sensing unit), and/or through sensors on a target. Moreover, the system 100 further provides the ability to provide feedback to both the test subject and/or clinician administering the test. The patient may further have access, in real-time, to their performance during the joint position error test and/or during a therapeutic exercise such as those described in connection with method 300C.

Figure 4A:
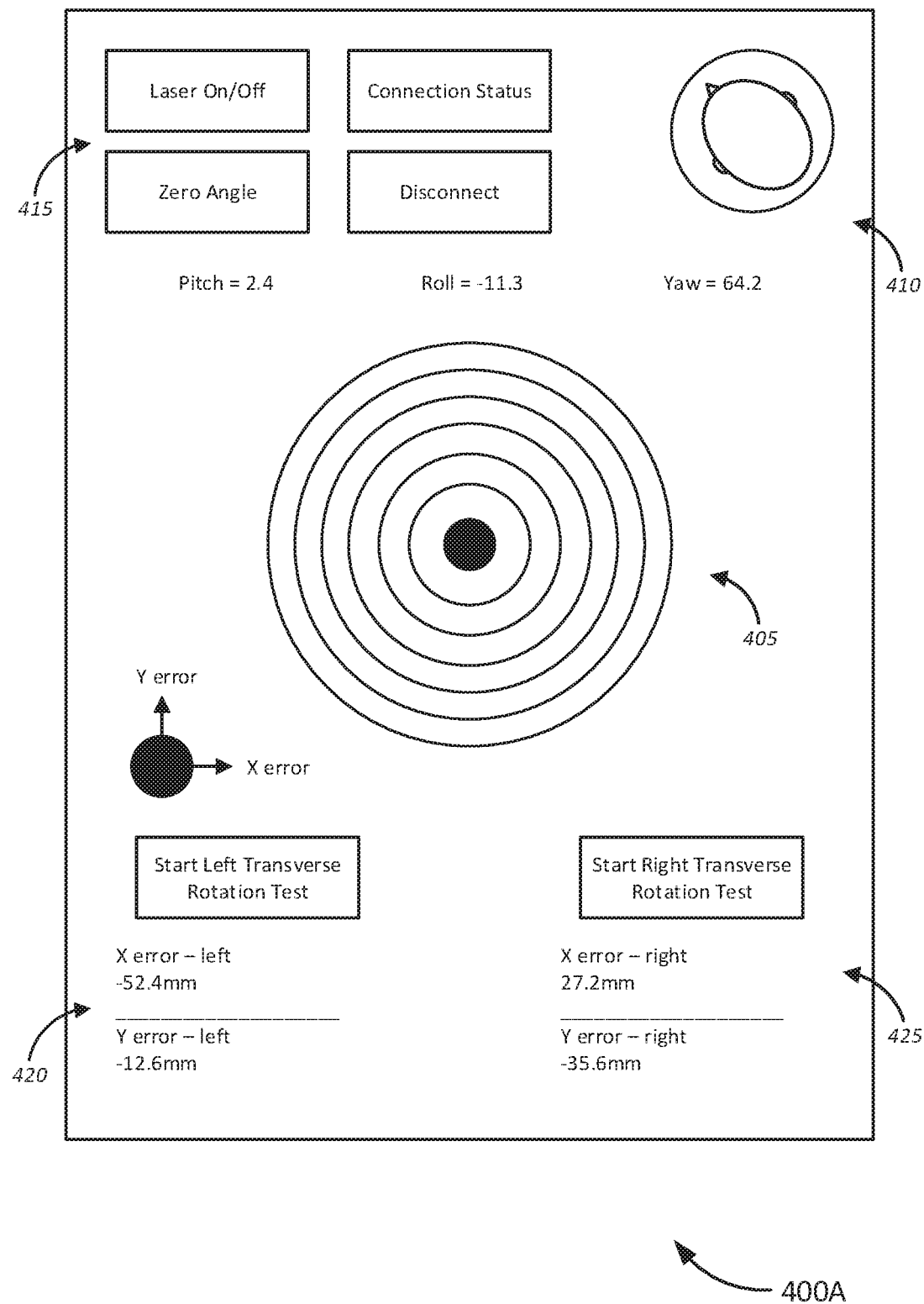
FIG. 4A is a diagram of a user interface for performing a joint position error test, in accordance with an embodiment.
Figure 4B:
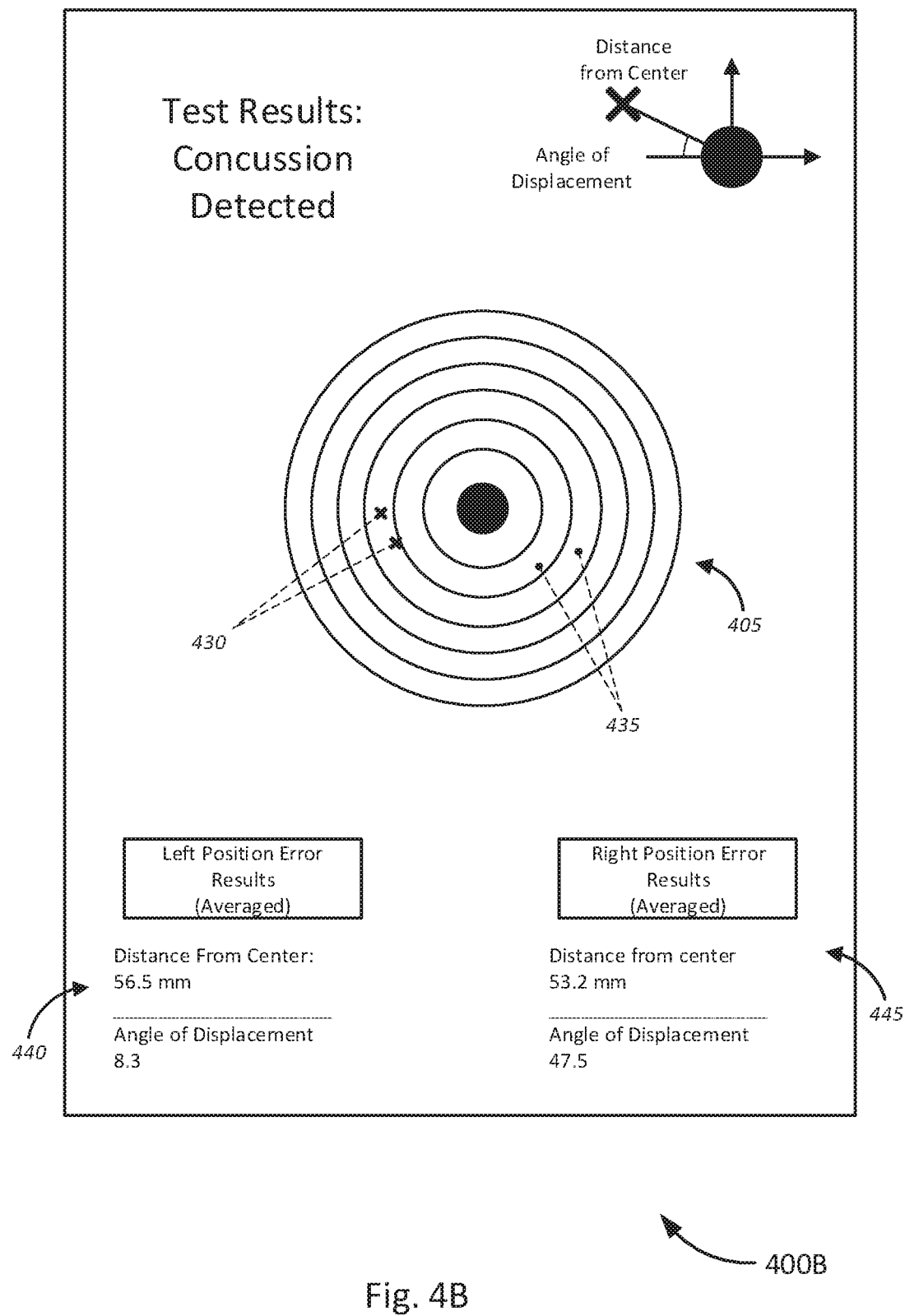
FIG. 4B is a diagram of the user interface presenting results of the joint position error test, in accordance with various embodiments.

FIGS. 4A and 4B depict respective user interfaces (UI) 400A, 400B for implementing a joint position error test, and presenting results of the joint position error test. In user interface 400A, an interface may be generated on a display unit, such as the display unit 140 of FIG. 1, and/or other display coupled to a joint position error processing unit and/or other user device, such as a smart phone or tablet computer. The UI 400A may include a representation of the target 405. The target 405, in this example, may be in the form of a bullseye. The UI 400A may include a live position information 410. Live position information 410 may include a schematic depiction of the test subject head's position and orientation, as well as relative angular position including pitch, roll, and yaw. The UI 400A may further include functional buttons 415. Functional buttons 415 may be configured to control the function of joint position error system, including a head sensing unit and/or joint position error processing unit. For example, the functional buttons 415 may be configured to disable or enable a light source, such as a laser. The functional buttons 415 may further include buttons to "zero" the angle (e.g., set a reference position), by resetting current positional measurements to 0. Functional buttons 415 may further indicate a connection status and provide the ability to manage connections within the system via the "Disconnect" button. For example, the "Disconnect" button may be configured to disconnect a user device from the head sensing unit and/or joint position error processing unit, or to disconnect the head sensing unit from the joint position error processing unit, etc.

In some embodiments, the UI 400A may further be configured to present current test information: left test information 420 and right test information 425. Left test information 420 may provide the ability to start and stop a left transverse rotation test, and to provide the results of a current left transverse rotation test, or a previous left transverse rotation test. For example, "X error—left" may display lateral displacement x after a left transverse rotation. "Y error—left" may display vertical displacement y after a left transverse rotation. Similarly, right test information 425 may provide the ability to start and stop a right transverse rotation test, and to provide the results of a current right transverse rotation test, or a previous right transverse rotation test.

The UI 400B may display a results page, with the results of a prediction and/or detection of a concussion. The representation of the target 405, may further include indicators indicative of one or more return position. Left return positions 430, indicated with an "x," may indicate return positions after a left transverse rotation. Correspondingly, right return positions 435, indicated with a dot, may indicate return positions after a right transverse rotation.

The UI 400B may further include test result information, such as averaged left position error results 440, and averaged right position error results 445. In the depicted example, and as previously described, the averaged left position error results 440 may report an averaged left absolute displacement from the reference position as 56.55 mm, and as determined as the average absolute displacements of the two left return positions 430. Similarly, the angle of displacement may be an averaged left total angular displacement of 8.3 degrees. For the right position error results 445, an averaged distance from center (e.g., averaged right absolute displacement) and an averaged angle of displacement (e.g., averaged right total angular displacement) may be reported, based on sensor data recorded at the two right return positions 435.

Figure 5A:
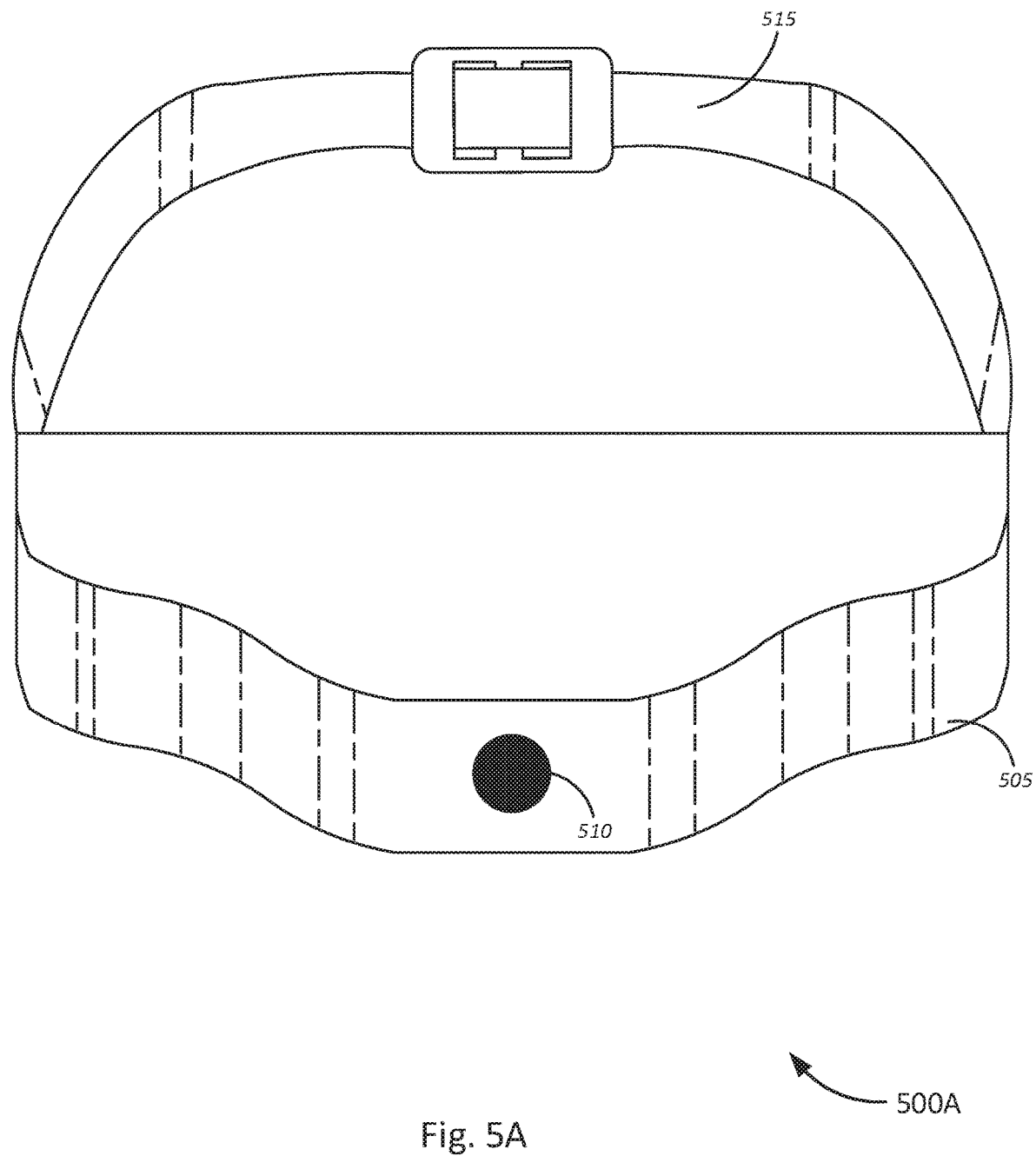
FIG. 5A is a perspective external view of a head sensing unit, in accordance with various embodiments.
Figure 5B:
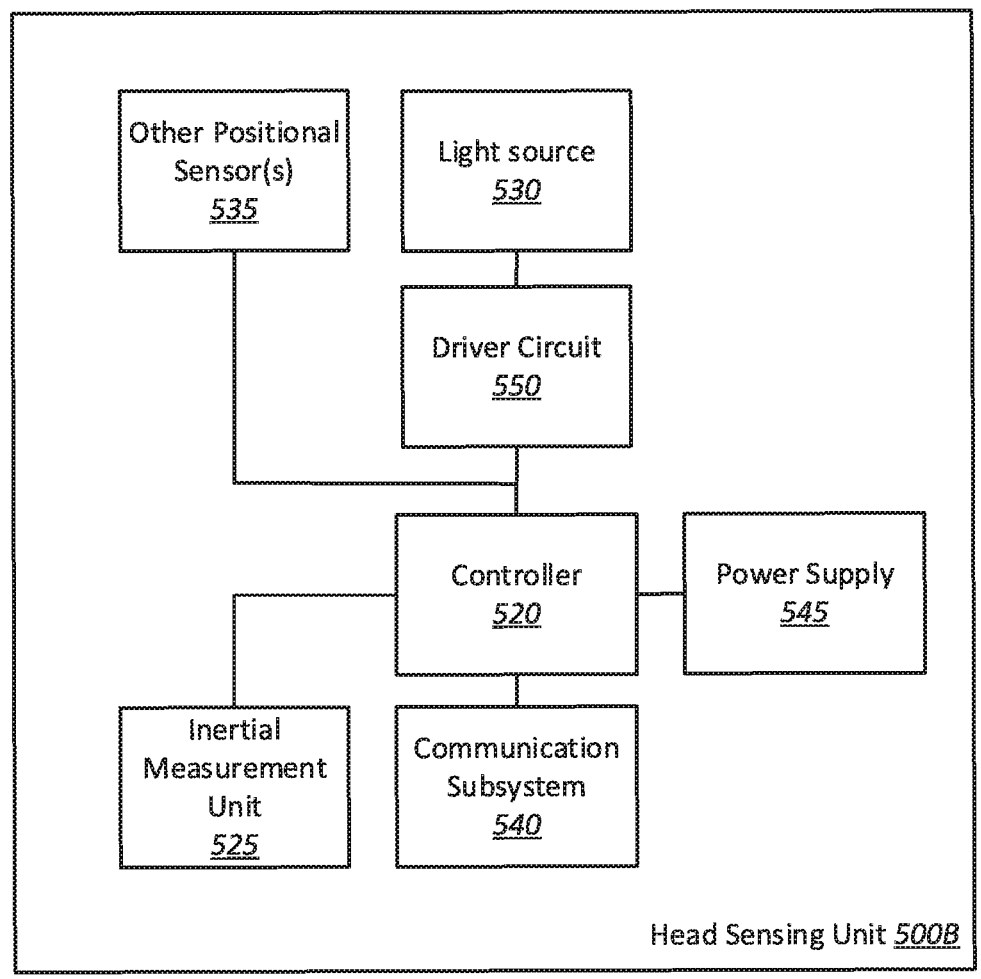
FIG. 5B is a schematic diagram of a head sensing unit, in accordance with various embodiments.

FIG. 5A is a perspective external view of one implementation of a head sensing unit 500A. In some embodiments, the head sensing unit 500A may include housing 505, a transmitter opening 510, and adjustable strap 515. FIG. 5B is a schematic block diagram of the various internal components of the head sensing unit 500B. The head sensing unit 500B may include a controller 520, IMU 525, light source 530, one or more other positional sensors 535, communication subsystem 540, power supply 545, and driver circuit 550. It should be noted that the various components of the head sensing unit 500 are schematically illustrated in FIGS. 5A and 5B, and that modifications to the components of the head sensing unit 500A and 500B may be possible in accordance with various embodiments.

In some embodiments, the head sensing unit 500A may be a self-contained headpiece for performing and implementing the functionalities detailed herein above. The housing 505 may, accordingly, be configured to internally house various components, including an IMU 525, or one or more other sensors 535 (e.g., MEMS, Bluetooth, or RF positional sensors), as previously described. For example, in some embodiments, a 3-axis MEMS gyroscope may be configured to measure the subject's head rotation and wirelessly may report the results via the communication subsystem 540.

As previously described, the housing 505 may further be configured to internally house a light source 530, such as a laser. In some embodiments, the laser or other light source 530 may be aligned with the transmitter opening 510 to allow a beam of light to pass through the housing and be projected onto a target. In some embodiments, the housing 505 may further include a camera, which may be configured to optically determine the difference between the starting orientation (e.g., a reference position) and an ending orientation (e.g., a return position) of the subject's head. The light source 530, in some embodiments, may further be coupled to a driver circuit 550. The head sensing unit 500A, 500B may, accordingly, further include a power supply 545 configured to sufficiently power the driving circuit 550 to drive the light source 530.

Sensor data obtained by the various positional sensors 525, 535 of the head sensing unit 500A may be transmitted to a joint position error processing unit via the communication subsystem 540 as previously described. In some further embodiments, the head sensing unit 500A may further process sensor data and transmit the results of a joint position error test (e.g., position error and/or averaged position error), which may then be transmitted to a joint position error processing unit, or to a display device.

Figure 6:
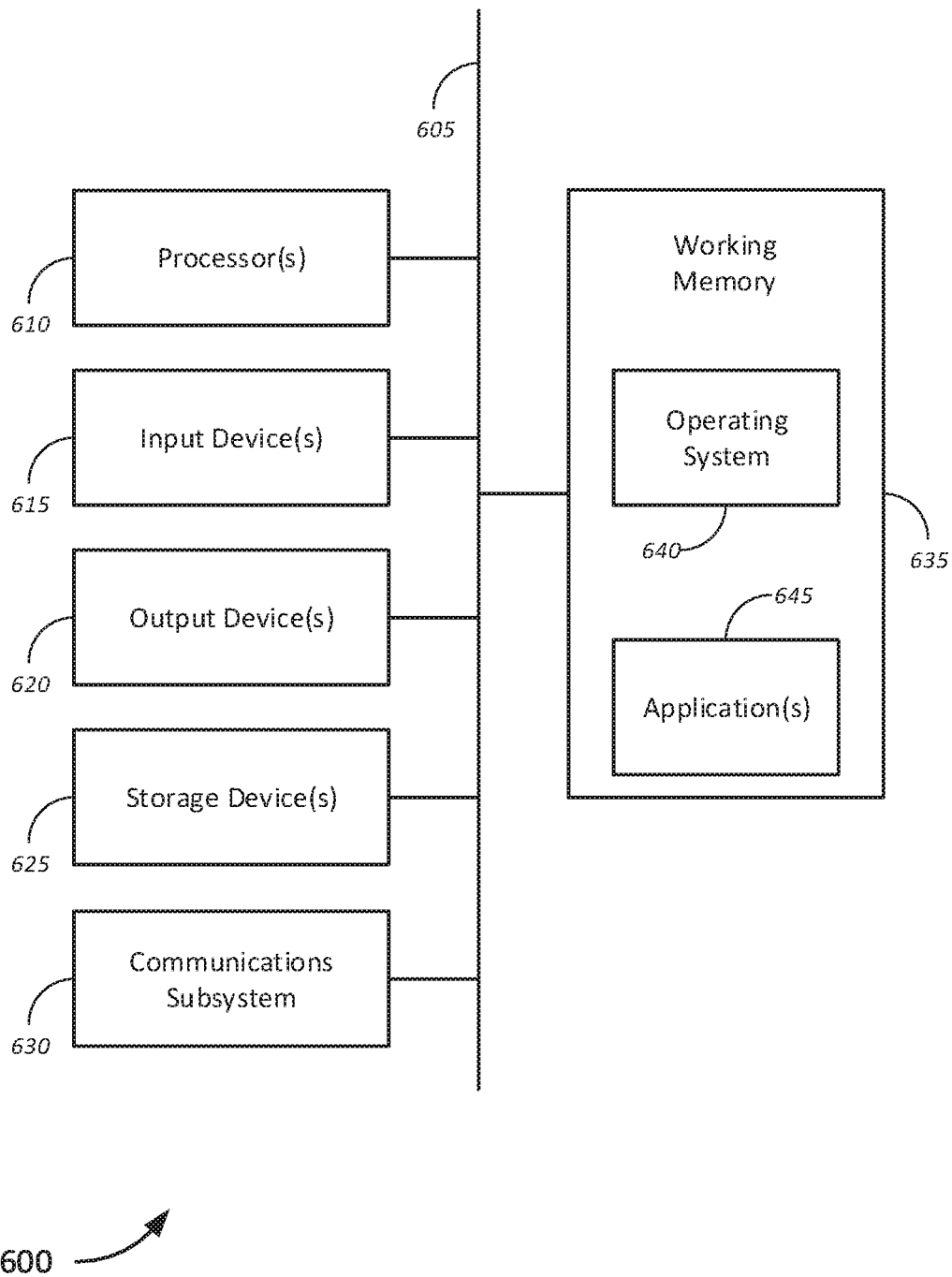
FIG. 6 is a schematic block diagram of a computer system for a joint position error test system, in accordance with various embodiments.

FIG. 6 is a schematic block diagram of a computer system 600 for a joint position error test system, in accordance with various embodiments. The computer system 600 is a schematic illustration of a computer system (physical and/or virtual), such as a head sensing unit and/or a joint position error processing unit, which may perform the methods provided by various other embodiments, as described herein. It should be noted that FIG. 6 provides a generalized illustration of various components, of which one or more of each may be utilized as appropriate. FIG. 6, therefore, broadly illustrates how individual system elements may be implemented in a relatively separated or relatively more integrated manner.

The computer system 600 includes multiple hardware (or virtualized) elements that may be electrically coupled via a bus 605 (or may otherwise be in communication, as appropriate). The hardware elements may include one or more processors 610, including, one or more general-purpose processors and/or one or more special-purpose processors (such as microprocessors, digital signal processing chips, graphics acceleration processors, and microcontrollers); one or more input devices 615, which include, for example, a mouse, a keyboard, one or more sensors, and/or the like; and one or more output devices 620, which can include a display device, and/or the like.

The computer system 600 may further include (and/or be in communication with) one or more storage devices 625, which can comprise local and/or network accessible storage, and/or can include a disk drive, a drive array, an optical storage device, solid-state storage device such as a random-access memory ("RAM") and/or a read-only memory ("ROM"), which can be programmable, flash-updateable, and/or the like. Such storage devices may be configured to implement any appropriate data stores, including various file systems, database structures, and/or the like.

The computer system 600 may also include a communications subsystem 630, which may include a modem, a network card (wireless or wired), an IR communication device, a wireless communication device and/or chipset (such as a Bluetooth™ device, an 802.11 device, a WiFi device, a WiMax device, a WWAN device, a low-power (LP) wireless device, a Z-Wave device, a ZigBee device, cellular communication facilities, etc.). The communications subsystem 630 may permit data to be exchanged with a network (such as the network described below, to name one example), with other computer or hardware systems, between data centers or different cloud platforms, and/or with any other devices described herein. In many embodiments, the computer system 600 further comprises a working memory 635, which can include a RAM or ROM device, as described above.

The computer system 600 also may comprise software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by various embodiments, as described herein. By way of example, one or more procedures described with respect to the method(s) discussed above may be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code may be encoded and/or stored on a non-transitory computer readable storage medium, such as the storage device(s) 625 described above. In some cases, the storage medium may be incorporated within a computer system, such as the system 600. In some embodiments, the storage medium may be separate from a computer system (i.e., a removable medium, such as a compact disc, etc.), and/or provided in an installation package, such that the storage medium can be used to program, configure, and/or adapt a general purpose computer with the instructions/code stored thereon. These instructions may take the form of executable code, which is executable by the computer system 600 and/or may take the form of source and/or installable code, which, upon compilation and/or installation on the computer system 600 (e.g., using any of a variety of generally available compilers, installation programs, compression/decompression utilities, etc.) then takes the form of executable code.

Substantial variations may be made in accordance with specific requirements. For example, customized hardware (such as programmable logic controllers, single board computers, FPGAs, ASICs, and SoCs) may also be used, and/or particular elements may be implemented in hardware, software (including portable software, such as applets, etc.), or both. Further, connection to other computing devices such as network input/output devices may be employed.

As mentioned above, in one aspect, some embodiments may employ a computer or hardware system (such as the computer system 600) to perform methods in accordance with various embodiments. According to various embodiments, some or all of the procedures of such methods are performed by the computer system 600 in response to processor 610 executing one or more sequences of one or more instructions (which may be incorporated into the operating system 640 and/or other code, such as an application program 645 or firmware) contained in the working memory 635. Such instructions may be read into the working memory 635 from another computer readable medium, such as one or more of the storage device(s) 625. By way of example, execution of the sequences of instructions contained in the working memory 635 may cause the processor(s) 610 to perform one or more procedures of the methods described herein.

The terms "machine readable medium" and "computer readable medium," as used herein, refer to any medium that participates in providing data that causes a machine to operate in a specific fashion. Various computer readable media may be involved in providing instructions/code to processor(s) 610 for execution and/or may be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 625. Volatile media includes dynamic memory, such as the working memory 635. In some embodiments, a computer readable medium may take the form of transmission media, which includes coaxial cables, copper wire and fiber optics, including the wires that comprise the bus 605, as well as the various components of the communication subsystem 630 (and/or the media by which the communications subsystem 630 provides communication with other devices). In some embodiments, transmission media can also take the form of waves (including, for example, radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 610 for execution. By way of example, the instructions may initially be carried on a magnetic disk and/or optical disc of a remote computer. A remote computer may load the instructions into its dynamic memory and send the instructions as signals over a transmission medium to be received and/or executed by the computer system 600. These signals, which may be in the form of electromagnetic signals, acoustic signals, optical signals, and/or the like, are all examples of carrier waves on which instructions can be encoded, in accordance with various embodiments.

The communications subsystem 630 (and/or components thereof) generally receives the signals, and the bus 605 then may carry the signals (and/or the data, instructions, etc. carried by the signals) to the working memory 635, from which the processor(s) 610 retrieves and executes the instructions. The instructions received by the working memory 635 may optionally be stored on a storage device 625 either before or after execution by the processor(s) 610.

Figure 7:
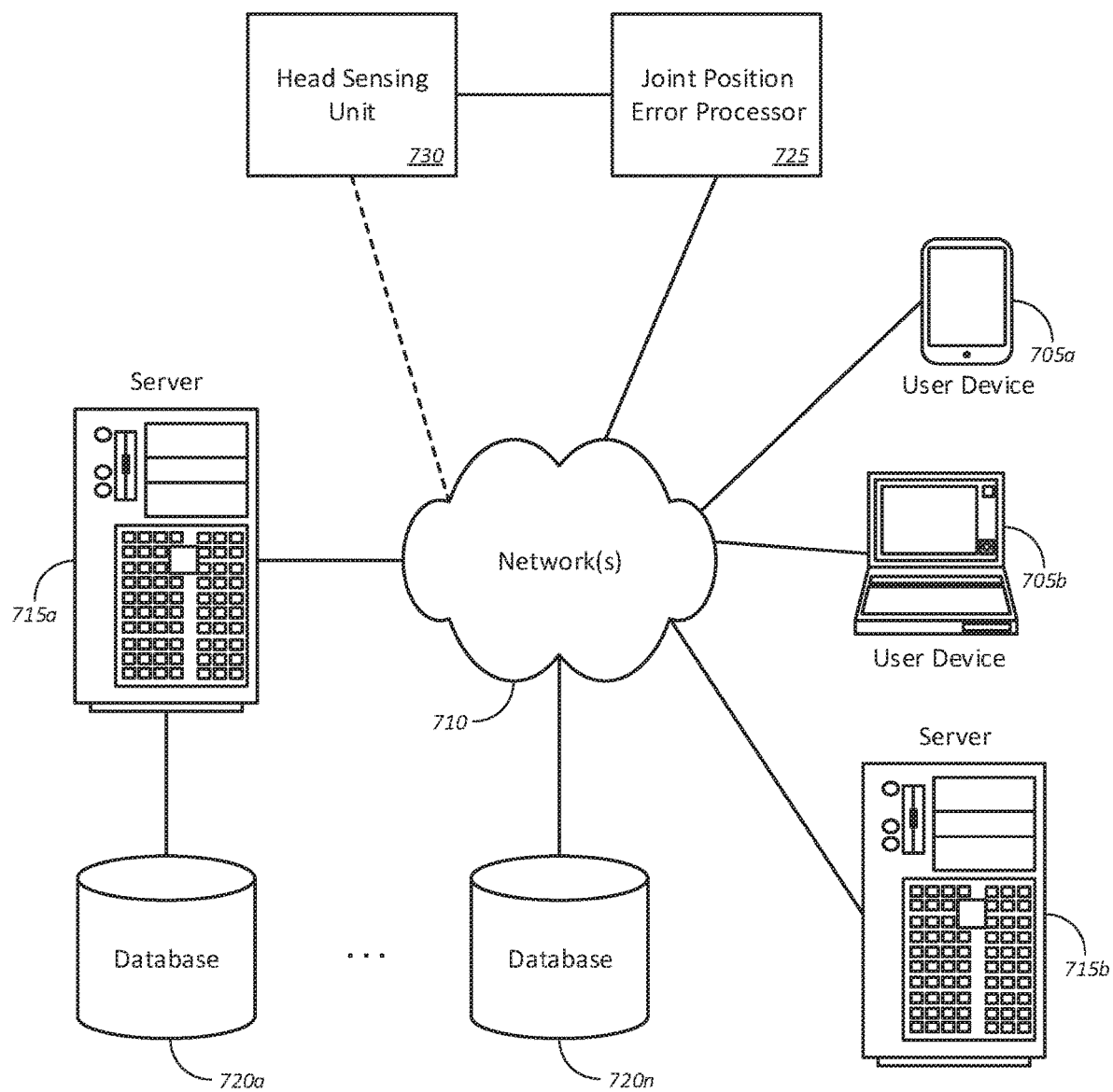
FIG. 7 is a schematic block diagram illustrating system of networked computer devices, in accordance with various embodiments.

FIG. 7 is a schematic block diagram illustrating system of networked computer devices, in accordance with various embodiments. The system 700 may include one or more user devices 705. A user device 705 may include, by way of example, desktop computers, single-board computers, tablet computers, laptop computers, handheld computers, edge devices, and the like, running an appropriate operating system. User devices 705 may further include external devices, remote devices, servers, and/or workstation computers running any of a variety of operating systems. A user device 705 may also have any of a variety of applications, including one or more applications configured to perform methods provided by various embodiments, as well as one or more office applications, database client and/or server applications, and/or web browser applications. A user device 705 may include any other electronic device, such as a thin-client computer, Internet-enabled mobile telephone, and/or personal digital assistant, capable of communicating via a network (e.g., the network(s) 710 described below) and/or of displaying and navigating web pages or other types of electronic documents. Although the system 700 is shown with two user devices 705a-705b, any number of user devices 705 may be supported.

Various embodiments operate in a networked environment, which can include a network(s) 710. The network(s) 710 can be any type of network that can support data communications, such as an access network, core network, or cloud network, and use any of a variety of protocols, including, for example, MQTT, CoAP, AMQP, STOMP, DDS, SCADA, XMPP, custom middleware agents, Modbus, BACnet, NCTIP, Bluetooth, Zigbee/Z-wave, TCP/IP, SNA™, IPX™, and the like. By way of example, the network(s) 710 can each include a local area network ("LAN"), including a fiber network, an Ethernet network, a Token-Ring™ network and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including a network operating under any of the IEEE 802.11 suite of protocols, the Bluetooth™ protocol, and/or any other wireless protocol; and/or any combination of these and/or other networks. In some embodiment, the network may include an access network of the service provider (e.g., an Internet service provider ("ISP")). In some embodiments, the network may include a core network of the service provider, backbone network, cloud network, management network, and/or the Internet.

Embodiments can also include one or more server computers 715. Each of the server computers 715 may be configured with an operating system, including any of those discussed above, as well as server operating systems. Each of the servers 715 may also be running one or more applications, which can be configured to provide services to one or more clients 705 and/or other servers 715.

By way of example, one of the servers 715 may be a data server, a web server, orchestration server, authentication server (e.g., TACACS, RADIUS, etc.), cloud computing device(s), or the like, as described above. The data server may include (or be in communication with) a web server, which can be used, by way of example, to process requests for web pages or other electronic documents from user computers 705. The web server can also run a variety of server applications, including HTTP servers, FTP servers, CGI servers, database servers, Java servers, and the like. In some embodiments, the web server may be configured to serve web pages that can be operated within a web browser on one or more of the user computers 705 to perform methods detailed herein.

The server computers 715, in some embodiments, may include one or more application servers, which can be configured with one or more applications, programs, web-based services, or other network resources accessible by a client. By way of example, the server(s) 715 can be one or more general purpose computers capable of executing programs or scripts in response to the user computers 705 and/or other servers 715, including web applications (which may, in some cases, be configured to perform methods provided by various embodiments). By way of example, a web application can be implemented as one or more scripts or programs written in any suitable programming language, such as Java™, C, C #™ or C++, and/or any scripting language, such as Perl, Python, or TCL, as well as combinations of any programming and/or scripting languages. The application server(s) can also include database servers, including those from Oracle™, Microsoft™, Sybase™, IBM™, and the like, which can process requests from clients (including, depending on the configuration, dedicated database clients, API clients, web browsers, etc.) running on a user computer, user device, or customer device 705 and/or another server 715.

In accordance with various embodiments, one or more servers 715 can function as a file server and/or can include one or more of the files (e.g., application code, data files, etc.) to implement various disclosed methods, incorporated by an application running on a user computer 705 and/or another server 715. A file server can include files, allowing such an application to be invoked remotely by a user computer, user device, or customer device 705 and/or server 715.

It should be noted that the functions described with respect to various servers herein (e.g., application server, database server, web server, file server, etc.) can be performed by a single server and/or a plurality of specialized servers, depending on implementation-specific parameters.

In some embodiments, the system can include one or more databases 720a-720n (collectively, "databases 720"). The location of each of the databases 720 is discretionary: by way of example, a database 720a may reside on a storage medium local to (and/or resident in) a server 715a (or, user device 705). A database 720n can be remote so long as it can be in communication (e.g., via the network 710) with one or more of these. In some embodiments, a database 720 can reside in a storage-area network ("SAN"). In some embodiments, the database 720 may be a relational database configured to host one or more data lakes collected from various data sources. The databases 720 may include SQL, no-SQL, and/or hybrid databases. The database may be controlled and/or maintained by a database server.

The system 700 may further include a joint position error processor 725 and head sensing unit 730. The joint position error processor 725 may be coupled to the network 710 and further to the head sensing unit 730. The head sensing unit 730 may also, in some examples, be coupled to the network 710. The head sensing unit 730 may be configured to determine a position and orientation of a test subject head in a reference position and return position, as previously described above. Sensor data taken at the reference position and return position may, according to some embodiments, be transmitted to the joint position error processor. As previously described, in some examples, a direct point-to-point connection may be established to transmit the sensor data from the head sensing unit 730 to the joint position error processor 725. In some embodiments, a networked connection may be utilized, such that sensor data may be transmitted from the head sensing unit 730 to the joint position error processor 725 via the network 710.

In some embodiments, as previously described, the results of the joint position error test may be compared to archived and/or historical data, and further compared to expected and/or normal ranges. In some embodiments, the joint position error processor 725, or in some embodiments, the head sensing unit 730, may be configured to obtain archived and/or historical data via the network 710, and from, for example, the one or more databases 720a-720n.

While certain features and aspects have been described with respect to embodiments described herein, numerous modifications are possible. For example, the methods and processes described herein may be implemented using hardware components, software components, and/or any combination thereof. Further, while various methods and processes described herein may be described with respect to certain structural and/or functional components for ease of description, methods provided by various embodiments are not limited to any single structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in sequentially for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a specific structural architecture and/or with respect to one system may be organized in alternative structural architectures and/or incorporated within other described systems. Hence, while various embodiments are described with—or without—certain features for ease of description and to illustrate aspects of those embodiments, the various components and/or features described herein with respect to one embodiment can be substituted, added and/or subtracted from among other described embodiments, unless the context dictates otherwise. Consequently, although several embodiments are described above, it will be appreciated that the present disclosure is intended to cover all modifications and equivalents within the scope of the following claims.

In the description, for the purposes of explanation, numerous specific details are set forth in order to provide a thorough understanding of the described embodiments. Other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered as incorporated to every embodiment of the present disclosure, as other embodiments of the present disclosure may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The various embodiments include, for example, methods, systems, and/or software products. By way of example, a method may comprise one or more procedures, any or all of which are executed by a computer system. Correspondingly, an embodiment may provide a computer system configured with instructions to perform one or more procedures in accordance with methods provided by various other embodiments. Similarly, a computer program may comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

Various modifications and additions can be made to the embodiments discussed without departing from the scope of the present disclosure. For example, while the embodiments described above refer to specific features, the scope of this present disclosure also includes embodiments having different combination of features and embodiments that do not include all the above described features.

What is claimed is:

1. A system comprising:
   a head sensing unit that includes one or more positional sensors and configured to be mechanically coupled with a head of a test subject;
   a controller communicatively coupled with the head sensing unit, the controller comprising:
      a processor; and
      non-transitory computer readable media comprising instructions executable by the processor to:
         obtain, via the head sensing unit, first sensor data from the one or more positional sensors at a first position, wherein the first sensor data is indicative of an orientation of the head of the test subject at the first position;
         obtain, via the head sensing unit, second sensor data from the one or more positional sensors at a second position, wherein the second sensor data is indicative of the orientation of the head of the test subject at the second position, wherein the second position is reached after the test subject has rotated the head to a third position and returned to the second position;
         determine a position error based on the first sensor data and the second sensor data, wherein the position error is indicative of a deviation of the orientation of the head of the test subject at the first position from the orientation of the head of the test subject at the second position; and
         determine a condition of the test subject based on the position error.

2. The system of claim 1, wherein the instructions are further executable by the processor to:
   determine that the head sensing unit has been aligned with an alignment area of a target; and receive first sensor data in response to a determination that the head sensing unit has been aligned with the alignment area of the target.

3. The system of claim 1, wherein the instructions are further executable by the processor to:
determine that the test subject has returned the head to the second position; and
obtain second sensor data in response to a determination that the test subject has returned the head to the second position.

4. The system of claim 1, wherein the head sensing unit further comprises a light source configured to project a beam of light onto a target, wherein the instructions to are further executable by the processor to:
determine that the beam of light has been aligned to be projected onto an alignment area of the target; and
obtain first sensor data in response to a determination that the beam of light has been aligned to be projected onto the alignment area.

5. The system of claim 1, wherein the instructions are further executable by the processor to:
instruct the test subject to rotate the head to the third position; and
instruct the test subject to return the head to the first position.

6. The system of claim 5, wherein instructing the test subject to rotate the head includes instructing the test subject to perform one of a transverse rotation, sagittal rotation, or coronal rotation.

7. The system of claim 5, wherein instructing the test subject to rotate the head further includes instructing the test subject to rotate the head to the left and right.

8. The system of claim 5, wherein instructing the test subject to rotate the head further includes instructing the test subject to rotate the head upward and downward.

9. The system of claim 1, wherein the instructions are further executable by the processor to:
determine, via the head sensing unit, whether the test subject has rotated the head, at the third position, beyond a threshold deviation from the first position.

10. The system of claim 1, wherein the position error includes one or more of an absolute displacement and a total angular displacement.

11. An apparatus comprising:
a processor; and
non-transitory computer readable media comprising instructions executable by the processor to:
determine, via a positional sensor, an orientation of a head of a test subject;
determine that the head of the test subject is in a first position;
obtain first sensor data from the positional sensor, wherein first sensor data is indicative of the orientation of the head of the test subject in the first position;
determine that the head of the test subject is in a second position after a rotation has been performed by the head of the test subject;
obtain second sensor data from the positional sensor, wherein second sensor data is indicative of the orientation of the head of the test subject in the second position; and
determine a position error based on the first sensor and the second sensor data, wherein the position error is indicative of a deviation of the orientation of the head of the test subject at the second position from the orientation of the head of the test subject at the first position.

12. The apparatus of claim 11, wherein the instructions are further executable by the processor to:
transmit, to a server computer, the first sensor data; and
transmit, to a server computer, the second sensor data.

13. The apparatus of claim 11, wherein the positional sensor is an inertial measurement unit.

14. The apparatus of claim 11 further comprising a light source, wherein the light source is configured to project a beam of light onto a target, wherein the instructions are further executable by the processor to:
determine that the beam of light has been aligned to be projected onto an alignment area of the target; and
obtain first sensor data in response to a determination that the beam of light has been aligned to be projected onto the alignment area.

15. The apparatus of claim 11, wherein the instructions are further executable by the processor to:
determine, via the positional sensor, whether the test subject has rotated the head beyond a threshold deviation from the first position; and
record the second sensor data in response to a determination that the test subject has rotated the head beyond the threshold deviation from the first position.

16. The apparatus of claim 11, wherein the instructions to determine that the head of the test subject is in one of the first position or the second position further comprises instructions executable by the processor to:
determine, via the positional sensor, that the test subject has stopped moving the head beyond a threshold range of positional change.

17. A method comprising:
determining, via one or more positional sensors, that a head of a test subject is in a first position;
obtaining first sensor data from the one or more positional sensors, wherein first sensor data is indicative of an orientation of the head of the test subject in the first position;
determining, via the one or more positional sensors, that the head of the test subject is in a second position;
obtaining second sensor data from the one or more positional sensors, where second sensor data is indicative of the orientation of the head of the test subject in the first position;
determining a position error based on the first sensor data and the second sensor data, wherein the position error is indicative of a deviation of the orientation of the head of the test subject at the second position from the orientation of the head of the test subject at the first position; and
determining a condition of the test subject based on the position error.

18. The method of claim 17, further comprising:
determining that an indicator is aligned with an alignment area of a target, wherein the indicator is visualization of an orientation of the head of the test subject, and the alignment area is indicative of a first position of the head of the test subject; and
recording first sensor data in response to a determination that the indicator has been aligned with the alignment area of the target.

19. The method of claim 17, further comprising:
generating instructions to the test subject to rotate the head; and determining, via the one or more positional sensors, whether the test subject has rotated the head beyond a threshold deviation from the first position.

* * * * *